US012167978B2

(12) United States Patent
Gutierrez

(10) Patent No.: US 12,167,978 B2
(45) Date of Patent: Dec. 17, 2024

(54) EYE MOUNTED DEVICE FOR THERAPEUTIC AGENT RELEASE

(71) Applicant: Verily Life Sciences LLC, Dallas, TX (US)

(72) Inventor: Christian Gutierrez, Pacifica, CA (US)

(73) Assignee: Verily Life Sciences LLC, Dallas, TX (US)

(*) Notice: Subject to any disclaimer, the term of this patent is extended or adjusted under 35 U.S.C. 154(b) by 253 days.

(21) Appl. No.: 17/858,452

(22) Filed: Jul. 6, 2022

(65) Prior Publication Data

US 2022/0339029 A1   Oct. 27, 2022

Related U.S. Application Data

(63) Continuation of application No. 16/736,423, filed on Jan. 7, 2020, now Pat. No. 11,399,976.
(Continued)

(51) Int. Cl.
*A61F 9/00* (2006.01)
*A61N 1/04* (2006.01)
*A61N 1/32* (2006.01)

(52) U.S. Cl.
CPC .......... *A61F 9/0017* (2013.01); *A61N 1/0436* (2013.01); *A61N 1/0448* (2013.01); *A61N 1/325* (2013.01)

(58) Field of Classification Search
CPC ... A61F 9/0017; A61K 9/0009; A61K 9/0048; A61K 9/0051; A61K 9/0097;
(Continued)

(56) References Cited

U.S. PATENT DOCUMENTS

| | | |
|---|---|---|
| 5,797,898 A | 8/1998 | Santini, Jr. et al. |
| 6,154,671 A | 11/2000 | Parel et al. |

(Continued)

FOREIGN PATENT DOCUMENTS

| | | |
|---|---|---|
| WO | 2006/047788 | 5/2006 |
| WO | 2007/050645 | 5/2007 |

(Continued)

OTHER PUBLICATIONS

PCT International Search Report and Written Opinion for corresponding International Application Serial No. PCT/US2020/012552, dated Apr. 17, 2020, pp. 1-17.
(Continued)

*Primary Examiner* — Deanna K Hall
(74) *Attorney, Agent, or Firm* — Haynes and Boone, LLP

(57) ABSTRACT

The present disclosure relates to devices and systems for targeted and controlled delivery of a therapeutic agent to a treatment site of an eye. Particularly, aspects are directed to a therapeutic agent delivery device that includes a polymeric substrate having a release region, a delivery region, and a receiving region; one or more reservoirs formed within the release region; a therapeutic agent disposed within the one or more reservoirs; an active, passive, or combination thereof controlled release mechanism for release of the therapeutic agent from the one or more reservoirs into the delivery region; and a circuit formed on the polymeric substrate, the circuit having a current source, a first iontophoresis electrode located within the delivery region for transport of the therapeutic agent from the delivery region into a target tissue via electromigration, and a second iontophoresis electrode located within the receiving region for maintaining electroneutrality within the tissue.

21 Claims, 17 Drawing Sheets

Related U.S. Application Data

(60) Provisional application No. 62/790,313, filed on Jan. 9, 2019.

(58) Field of Classification Search
CPC .. A61N 1/0428; A61N 1/0436; A61N 1/0448; A61N 1/303; A61N 1/325; G02C 7/04
See application file for complete search history.

(56) References Cited

U.S. PATENT DOCUMENTS

| | | |
|---|---|---|
| 6,319,240 B1 | 11/2001 | Beck |
| 6,544,193 B2 | 4/2003 | Abreu |
| 8,529,538 B2 | 9/2013 | Pang et al. |
| 11,399,976 B2 | 8/2022 | Gutierrez |
| 2002/0188282 A1 | 12/2002 | Greenberg |
| 2006/0088515 A1 | 4/2006 | Higuchi et al. |
| 2007/0123814 A1 | 5/2007 | Roy |
| 2007/0260171 A1 | 11/2007 | Higuchi et al. |
| 2008/0168921 A1 | 7/2008 | Uhland et al. |
| 2011/0144619 A1 | 6/2011 | Meng et al. |
| 2014/0207048 A1 | 7/2014 | Dipierro et al. |
| 2014/0228783 A1 | 8/2014 | Kraft |
| 2016/0175148 A1 | 6/2016 | De Sousa Martins et al. |

FOREIGN PATENT DOCUMENTS

| | | |
|---|---|---|
| WO | 2009/086112 | 7/2009 |
| WO | 2016/0118933 | 7/2016 |
| WO | 2018/064377 | 4/2018 |

OTHER PUBLICATIONS

PCT International Search Report and Written Opinion for corresponding International Application Serial No. PCT/US2020/12548, dated Jun. 24, 2020, pp. 1-23.
International Application No. PCT/US2020/012548, International Search Report and Written Opinion, Jun. 24, 2020, 23 pages.
International Application No. PCT/US2020/012548, "Invitation to Pay Additional Fees and, Where Applicable, Protest Fee", Apr. 3, 2020, 16 pages.
International Preliminary Report on Patentability received for PCT Patent Application No. PCT/US20/12552, mailed on Jul. 22, 2021, 12 pages.
Notice of Allowance received for U.S. Appl. No. 16/736,423, mailed on Mar. 30, 2022, 8 pages.
Office Action received for Brazil Patent Application No. 112021013455, mailed on Apr. 29, 2024, 3 pages of Original document only.
Requirement for Restriction/Election received for U.S. Appl. No. 16/736,423, mailed on Nov. 4, 2021, 6 pages.

EYE MOUNTED DEVICE FOR THERAPEUTIC AGENT RELEASE

CROSS-REFERENCE TO RELATED APPLICATION

The present application is a continuation application of U.S. patent application Ser. No. 16/736,423, filed 7 Jan. 2020, which claims the benefit of U.S. Provisional Application No. 62/790,313, filed 9 Jan. 2019. The entirety of these applications is hereby incorporated by reference by all purposes.

FIELD OF THE INVENTION

The present disclosure relates to delivery of a therapeutic agent, and more particularly to devices and systems for targeted and controlled delivery of a therapeutic agent to a treatment site of an eye.

BACKGROUND

Medical treatment often requires the administration of a therapeutic agent (e.g., medicament, chemicals, small-molecule drugs, genes, etc.) to a specific area of the patient's body. A significant challenge that most therapeutic agents face is their inability to be delivered to the specific area in an effective manner. In traditional therapeutic agent delivery systems such as oral ingestion (e.g., solid or liquid forms), inhalants, or intravascular injection, the therapeutic agent is distributed systemically through the body via the circulatory, pulmonary, or lymphatic system. For most therapeutic agents, only a small portion of the agent reaches the specific area or diseased tissue to be affected, such as in chemotherapy where a substantial portion (e.g., about 99%) of the therapeutic agent administered to a patient does not reach the tumor site.

In contrast to traditional systemic delivery systems, targeted therapeutic agent delivery seeks to concentrate the agent in the area or tissues of interest while reducing the relative concentration of the agent in the remaining tissues. The goal of a targeted therapeutic agent delivery system is to prolong, localize, target and have a protected therapeutic agent interaction with the diseased tissue (specific part of the body). Some diseases, however, are difficult to treat with currently available therapies and/or require administration of drugs to anatomical regions to which access is difficult to achieve. A patient's eye is a prime example of a difficult-to-reach anatomical region, and many ocular diseases, including retinitis pigmentosa, age-related macular degeneration (AMD), diabetic retinopathy, and glaucoma, are difficult to treat with many of the currently available therapies.

Over the last several decades a multitude of approaches involving both therapeutic agent formulation and delivery system development have been undertaken to address these ocular diseases. Despite significant advances in the development of therapeutic agents, the currently available devices and systems for delivery of the therapeutic agents are limited to two primary routes of administration: 1) topical eye drops, and 2) intravitreal needle injection. Both of these administration options, while effective if regimens are strictly maintained, ultimately fail in providing long-term curative outcomes for patients, primarily due to deficiencies in maintaining localization of the therapeutic agent at the treatment site of the eye and a lack of compliance by the patient in administration of the therapeutic agent. Accordingly, improved methods of ocular therapeutic agent delivery are required to address the shortcomings of topical eye drops and intravitreal injections.

BRIEF SUMMARY

In various embodiments, a therapeutic agent delivery device is provided that comprises: a polymeric substrate comprising a release region, a delivery region, and a receiving region; one or more reservoirs formed within the release region of the polymeric substrate; a therapeutic agent disposed within the one or more reservoirs; an active, passive, or combination thereof controlled release mechanism for release of the therapeutic agent from the one or more reservoirs into the delivery region, where the controlled release mechanism is located within the release region, and the release region is in fluidic communication with the delivery region; and a circuit formed on the polymeric substrate, the circuit comprising a current source, a first iontophoresis electrode located within the delivery region for transport of the therapeutic agent from the delivery region into a target tissue via electromigration, and a second iontophoresis electrode located within the receiving region for maintaining electroneutrality within the tissue.

In some embodiments, the polymeric substrate is formed of polyimide, liquid crystal polymer, parylene, polyether ether ketone, polyethylene terephthalate, poly(methyl methacrylate), polyurethane, rigid gas permeable fluorosilicone acrylate, a silicon-based polymer, a silicone acrylate, cyclic olefin co-polymer (COP/COC), hydrogel, or a combination thereof.

In some embodiments, the release region and the delivery region at least partially overlap or are otherwise co-located within the polymeric substrate. In other embodiments, the release region is located separately from the delivery region within the polymeric substrate. Optionally, at least a portion of the delivery region is exposed to an environment external to the polymeric substrate. Optionally, the receiving region is located separately from the delivery region within the polymeric substrate.

In some embodiments, the therapeutic agent delivery device further comprises an overmold polymeric layer formed around substantially an entirety of the polymeric substrate. Optionally, the overmold polymeric layer is formed of polymethylmethacrylate, polyhydroxyethylmethacrylate, a hydrogel, a silicon-based polymer, a silicone elastomer, or a combination thereof.

In some embodiments, the first iontophoresis electrode is located under the one or more reservoirs formed within the release region of the polymeric substrate. In certain embodiments, the first iontophoresis electrode is a silver (Ag) anode and the second iontophoresis electrode is a silver chloride (AgCl) cathode.

In some embodiments, the controlled release mechanism is a polymeric layer. Optionally, the polymeric layer is formed of polymethylmethacrylate, polyhydroxyethylmethacrylate, a hydrogel, a silicon-based polymer, a silicone elastomer, or a combination thereof. In some embodiments, the controlled release mechanism is a valve. Optionally, the valve is a metallic thin film electrically connected to the current source.

In some embodiments, the polymeric substrate has an average thickness between 0.01 mm and 2 mm, and a semi-circle shape. In other embodiments, the polymeric substrate has an average thickness between 0.01 mm and 2 mm, and a donut shape.

In some embodiments, the therapeutic agent delivery device further comprises a counter ion disposed within the one or more reservoirs or the delivery region, where the therapeutic agent is ionized and the counter ion has a charge opposite that of the therapeutic agent.

In various embodiments, a therapeutic agent delivery device is provided that comprises: a substrate comprising a distal surface and a proximal surface with one or more layers of polymer disposed therebetween; a reservoir formed within the one or more layers of polymer, where the reservoir comprises a holding chamber for a therapeutic agent, an egress, and an active, passive, or combination thereof controlled release mechanism that temporarily blocks passage of the therapeutic agent from the holding chamber through the egress; an anode chamber formed within the one or more layers of polymer and in fluidic communication with the reservoir, where a portion of the anode chamber is exposed to an environment outside of the substrate at the distal surface, and the anode chamber comprises a first iontophoresis electrode; a cathode chamber formed within the one or more layers of the polymer, where a portion of the cathode chamber is exposed to the environment outside of the substrate at the distal surface, the cathode chamber is spaced at least a predetermined distance from the anode chamber, and the cathode chamber comprises a second iontophoresis electrode; and a circuit formed on or within the one or more layers of the polymer, the circuit comprising a current source, the first iontophoresis electrode, and the second iontophoresis electrode.

In some embodiments, the therapeutic agent delivery device further comprises: one or more processors formed on or within the one or more layers of the polymer and electrically connected to the current source; a battery formed on or within the one or more layers of the polymer and electrically connected to the current source; and an antenna formed on or within the one or more layers of the polymer and electrically connected to the one or more processors.

In some embodiments, the first iontophoresis electrode is a silver (Ag) anode and the second iontophoresis electrode is a silver chloride (AgCl) cathode.

In some embodiments, the therapeutic agent delivery device further comprises a counter ion disposed within the reservoir or the anode chamber, where the therapeutic agent is ionized and the counter ion has a charge opposite that of the therapeutic agent.

In some embodiments, the therapeutic agent delivery device further comprises an overmold polymeric layer formed around substantially an entirety of the substrate. In some embodiments, the therapeutic agent delivery device has an average thickness between 0.01 mm and 3 mm. In some embodiments, the substrate has an average thickness between 0.01 mm and 2 mm.

In some embodiments, the reservoir and the anode chamber at least partially overlap or are otherwise co-located within the one or more layers of polymer. In other embodiments, the reservoir is located separately from the anode chamber within the one or more layers of polymer.

In some embodiments, the therapeutic agent delivery device further comprises a plurality of anode electrodes disposed with the anode chamber, where the first iontophoresis electrode is one of the plurality of anode electrodes.

In some embodiments, the therapeutic agent delivery device further comprises: a plurality of reservoirs formed within the one or more layers of polymer, where the reservoir is one of the plurality of reservoirs; and a plurality of anode chambers formed within the one or more layers of polymer, where the anode chamber is one of the plurality of anode chambers. Optionally, each anode chamber of the plurality of anode chambers at least partially overlaps or is otherwise co-located with each reservoir of the plurality of reservoirs, respectively.

In some embodiments, a first type of therapeutic agent is disposed within a first subset of the plurality of reservoirs, a second type of therapeutic agent is disposed within a second subset of the plurality of reservoirs, and the therapeutic agent is of the first type of therapeutic agents.

In some embodiments, the therapeutic agent delivery device further comprises a plurality of cathode chambers formed within the one or more layers of the polymer, where the cathode chamber is one of the plurality of cathode chambers, and each of the plurality of cathode chambers is spaced at least the predetermined distance from the anode chamber.

In some embodiments, the controlled release mechanism is a polymeric layer, a valve, or a combination thereof. Optionally, the polymeric layer is formed of polymethylmethacrylate, polyhydroxyethylmethacrylate, a hydrogel, a silicon-based polymer, a silicone elastomer, or a combination thereof. Optionally, the valve is a metallic thin film electrically connected to the current source.

In various embodiments, a therapeutic agent delivery device is provided that comprises: a polymeric substrate comprising a release region, a delivery region, and a receiving region, where the release region is in fluidic communication with the delivery region; a first set of reservoirs formed within a first portion of the release region of the polymeric substrate; a first type of therapeutic agent disposed within the first set of reservoirs; a second set of reservoirs formed within a second portion of the release region of the polymeric substrate; a second type of therapeutic agent disposed within the second set of reservoirs; a first active, passive, or combination thereof controlled release mechanism for release of the first type of therapeutic agent from the first set of reservoirs into a first portion of the delivery region, where the first controlled release mechanism is located within the first portion of the release region; a second active, passive, or combination thereof controlled release mechanism for release of the second type of therapeutic agent from the second set of reservoirs into a second portion of the delivery region, where the second controlled release mechanism is located within the second portion of the release region; and a circuit formed on the polymeric substrate, the circuit comprising a current source, a first set of iontophoresis electrodes located within the first portion of the delivery region for transport of the first type of therapeutic agent from the first portion of the delivery region into a target tissue via electromigration, a second set of iontophoresis electrodes located within the second portion of the delivery region for transport of the second type of therapeutic agent from the second portion of the delivery region into the target tissue via electromigration, and an iontophoresis electrode located within the receiving region for maintaining electroneutrality within the tissue.

In some embodiments, the polymeric substrate is formed of polyimide, liquid crystal polymer, parylene, polyether ether ketone, polyethylene terephthalate, poly(methyl methacrylate), polyurethane, rigid gas permeable fluorosilicone acrylate, a silicon-based polymer, a silicone acrylate, cyclic olefin co-polymer (COP/COC), hydrogel, or a combination thereof.

In some embodiments, the release region and the delivery region at least partially overlap and are co-located on the polymeric substrate. In other embodiments, the release region is located separately from the delivery region on the polymeric substrate.

In some embodiments, at least a portion of the delivery region is exposed to an environment external to the polymeric substrate. In some embodiments, the receiving region is located separately from the delivery region on the polymeric substrate.

In some embodiments, the therapeutic agent delivery device further comprises an overmold polymeric layer formed around substantially an entirety of the polymeric substrate. Optionally, the overmold polymeric layer is formed of polymethylmethacrylate, polyhydroxyethylmethacrylate, a hydrogel, a silicon-based polymer, a silicone elastomer, or a combination thereof.

In some embodiments, the first set of iontophoresis electrodes are located under the first set of reservoirs and the second set of iontophoresis electrodes are located under the second set of reservoirs. In some embodiments, the first set of iontophoresis electrodes and the second set of iontophoresis electrodes are silver (Ag) anodes and the iontophoresis electrode located within the receiving region is a silver chloride (AgCl) cathode.

In some embodiments, the first controlled release mechanism is a polymeric layer, a valve, or a combination thereof. In some embodiments, the second controlled release mechanism is a polymeric layer, a valve, or a combination thereof. Optionally, the polymeric layer is formed of polymethylmethacrylate, polyhydroxyethylmethacrylate, a hydrogel, a silicon-based polymer, a silicone elastomer, or a combination thereof. Optionally, the valve is a metallic thin film electrically connected to the current source.

In some embodiments, the polymeric substrate has an average thickness between 0.01 mm and 2 mm, and a semi-circle shape. In some embodiments, the polymeric substrate has an average thickness between 0.01 mm and 2 mm, and a donut shape.

In some embodiments, the therapeutic agent delivery device further comprises: a first type of counter ion disposed within the first set of reservoirs or the first portion of the delivery region, where the first type of therapeutic agent is ionized and the first type of counter ion has a charge opposite that of the first type of therapeutic agent; and a second type of counter ion disposed within the second set of reservoirs or the second portion of the delivery region, where the second type of therapeutic agent is ionized and the second type of counter ion has a charge opposite that of the second type of therapeutic agent.

In various embodiments, a system is provided that comprises: one or more processors formed on a polymeric substrate; and a memory formed on the polymeric substrate, the memory coupled to the one or more processors, the memory storing a plurality of instructions executable by the one or more processors, the plurality of instructions comprising instructions that when executed by the one or more processors cause the one or more processors to perform processing comprising: releasing, by a controlled release mechanism, a therapeutic agent from one or more reservoirs formed within a release region of the polymeric substrate into a delivery region of the polymeric substrate; applying, by a controller, a potential to a circuit formed on the polymeric substrate to create a current flowing through the circuit, where the circuit comprises a current source, a first iontophoresis electrode located within the delivery region, and a second iontophoresis electrode located within a receiving region of the polymeric substrate; electromigrating, by the first iontophoresis electrode, the therapeutic agent from the delivery region to a tissue based on the current flowing through the circuit; and maintaining, by the second iontophoresis electrode, electroneutrality within the tissue based on the current flowing through the circuit.

In some embodiments, the releasing comprising applying, by the controller, another potential to the controlled release mechanism.

In some embodiments, the process further comprises: releasing, by the controlled release mechanism, a different therapeutic agent from the one or more reservoirs formed within the release region of the polymeric substrate into the delivery region of the polymeric substrate; applying, by the controller, a subsequent potential to the circuit formed on the polymeric substrate to create a subsequent current flowing through the circuit; electromigrating, by the first iontophoresis electrode, a different therapeutic agent from the delivery region to the tissue based on the subsequent current flowing through the circuit; and maintaining, by the second iontophoresis electrode, electroneutrality within the tissue based on the subsequent current flowing through the circuit.

In some embodiments, the process further comprises releasing, by the controlled release mechanism, a different therapeutic agent from the one or more reservoirs formed within the release region of the polymeric substrate into the delivery region of the polymeric substrate, where the applying the potential to the circuit causes the electromigrating, by the first iontophoresis electrode, the different therapeutic agent from the delivery region to the tissue based on the current flowing through the circuit.

BRIEF DESCRIPTION OF THE DRAWINGS

The present invention will be better understood in view of the following non-limiting figures, in which.

DETAILED DESCRIPTION

I. Introduction

The following disclosure describes devices and systems for targeted and controlled delivery of a therapeutic agent to a treatment site of an eye. As used herein, the phrase "targeted" or "targeted delivery" refers to a technique of delivering a therapeutic agent to a subject in a localized manner that increases a concentration of the therapeutic agent at a treatment site of the subject relative to areas outside of the treatment site. As used herein, the term "controlled" or "controlled delivery" refers to a technique of delivering a therapeutic agent to a subject locally or systemically at a predetermined rate for a specified period of time. As used herein, the term "therapeutic agent" or "agent" comprises any desired pharmaceutical agent or mixture of individual pharmaceutical agents or the like, for the administration of one or more active agents to a region of a patient. In various embodiments, the therapeutic agent delivery devices or systems are designed to be placed on a surface (e.g., a corneal or scleral surface) of the eye for targeted and controlled delivery of a therapeutic agent to a treatment site of an eye. The therapeutic agent delivery devices or systems comprise reservoir(s) housing a therapeutic agent in one or more physical forms including aqueous (liquid), gel, dry (powder), or other combinations thereof. The reservoir(s) provide a means for temporary storage of the therapeutic agent prior to release and delivery to a treatment site. In some embodiments, the release and delivery of the therapeutic agent is actively, passively, or a combination thereof, controlled by one or more mechanisms to achieve fully customizable targeted therapeutic agent delivery regimes that drastically increase residence time of the therapeutic agent in the region of interest (e.g., the sclera, outer cornea, posterior segment, etc.) from about 30 seconds to greater than 30 minutes when compared to topical administration such as eye drops.

Figure 1A:
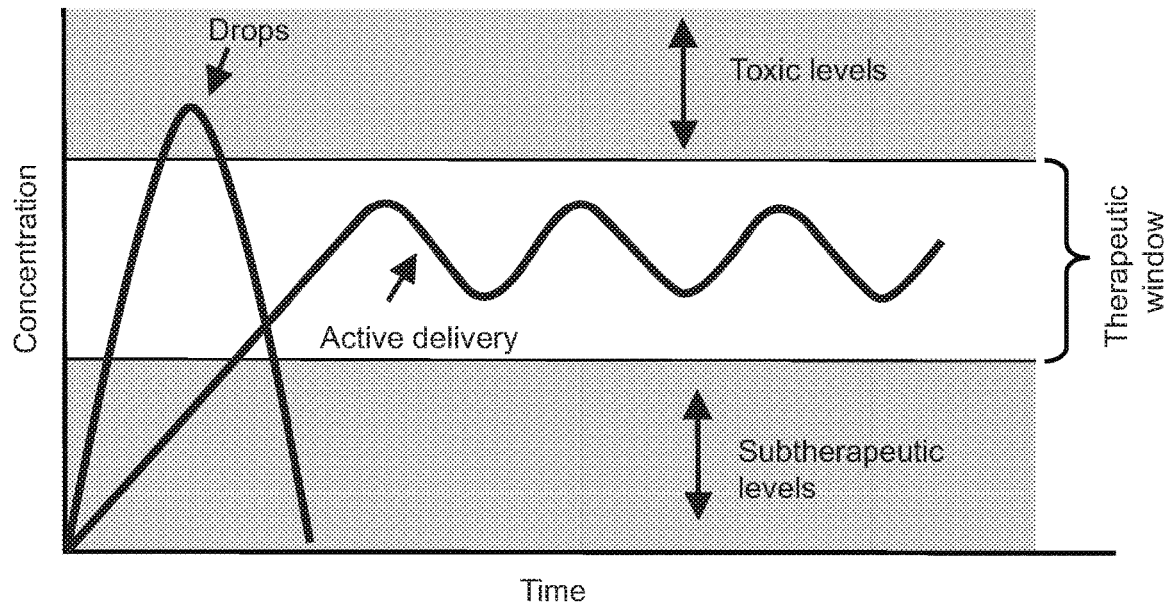
FIG. 1A shows a diagram depicting topical, injection, and active drug delivery modalities in accordance with various embodiments.
Figure 1B:
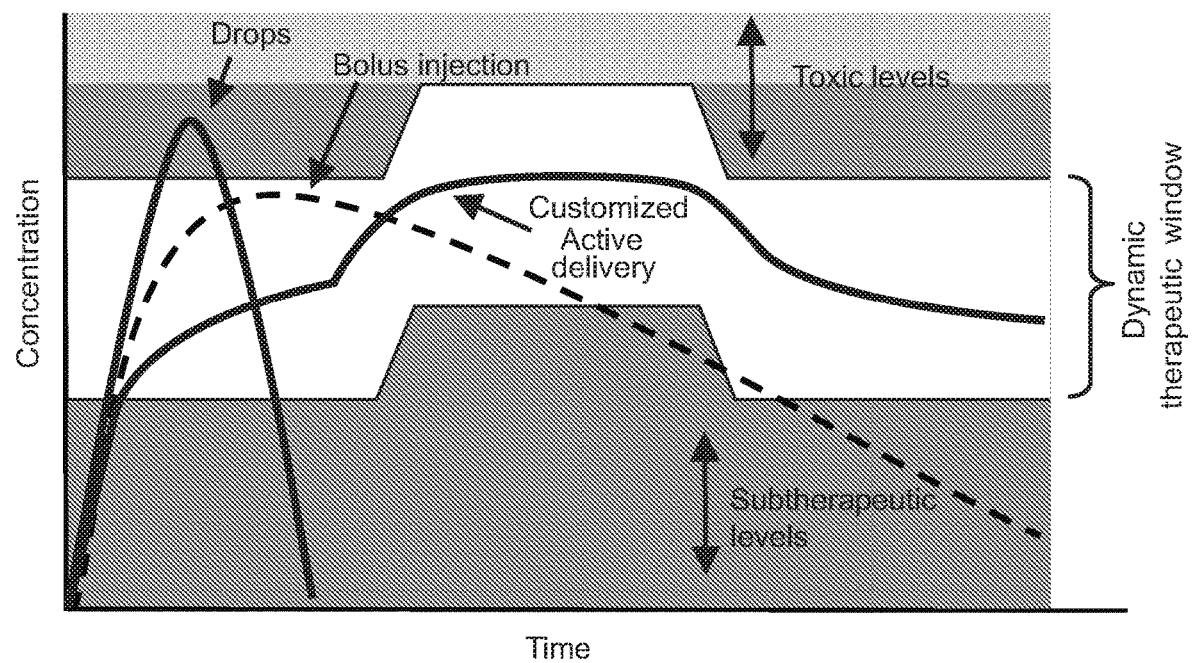
FIG. 1B shows a diagram depicting topical, injection, and active drug delivery modalities with a dynamic therapeutic window in accordance with various embodiments.

A problem associated with conventional systems and devices for targeted ocular therapeutic agent delivery (i.e., 1) topical eye drops and 2) intravitreal needle injection), is compliance and customized delivery profiles. For example, conventional systems and devices for targeted ocular therapeutic agent delivery ultimately fail in providing long-term curative outcomes for patients, primarily due to a lack of compliance, and assistive agent administration technologies that help patients achieve compliance are needed. Moreover, conventional systems and devices rely on patient assisted procedures (e.g., eye drops) or out-patient procedures (e.g., needle injections) with no active control of dosage or delivery, and thus lack the ability to implement patient-specific treatment. FIG. 1A shows a diagram depicting topical, injection, and active drug delivery modalities. Compared to conventional agent administration approaches, the active delivery is ideally suited to maintaining physiologically relevant concentrations in the therapeutic window. FIG. 1B shows a diagram depicting topical, injection, and active drug delivery modalities with a dynamic therapeutic window. Compared to conventional agent administration approaches, active delivery is the only method capable of maintaining physiologically relevant concentrations in conditions with a time-varying therapeutic window.

To address these problems, the present embodiments are directed to therapeutic agent delivery devices or systems that comprise one or more mechanisms to control the release and delivery of the therapeutic agent to achieve fully customizable targeted therapeutic agent delivery regimes. In an illustrative embodiments, a therapeutic agent delivery device is provided that comprises: a polymeric substrate comprising a release region, a delivery region, and a receiving region; one or more reservoirs formed within the release region of the polymeric substrate; a therapeutic agent disposed within the one or more reservoirs; an active, passive, or combination thereof controlled release mechanism for release of the therapeutic agent from the one or more reservoirs into the delivery region, where the controlled release mechanism is located within the release region, and the release region is in fluidic communication with the delivery region; and a circuit formed on the polymeric substrate, the circuit comprising a current source, a first iontophoresis electrode located within the delivery region for transport of the therapeutic agent from the delivery region into a target tissue via electromigration, and a second iontophoresis electrode located within the receiving region for maintaining electroneutrality within the tissue.

Advantageously, these approaches provide therapeutic agent delivery devices or systems, which have no moving parts, increases residence time of the agent in the region of interest, and improve bioavailability in the anterior or posterior segment via transscleral or transcorneal delivery. Additionally, these approaches provide therapeutic agent delivery devices or systems capable of achieving fully customizable drug release regimes from first-order constant release profiles to on-demand pulsatile release, which delivers acceptable concentrations of agent to intraocular tissue safely, while minimizing the systemic exposure to the agent. It should be understood that although therapeutic agent delivery devices or systems designed for the eye are provided as examples of various embodiments, this solution is applicable to other tissues that could benefit from targeted and controlled delivery of a therapeutic agent.

II. Therapeutic Agent Delivery Devices

Sclera Therapeutic Agent Release Device

Figure 2A:
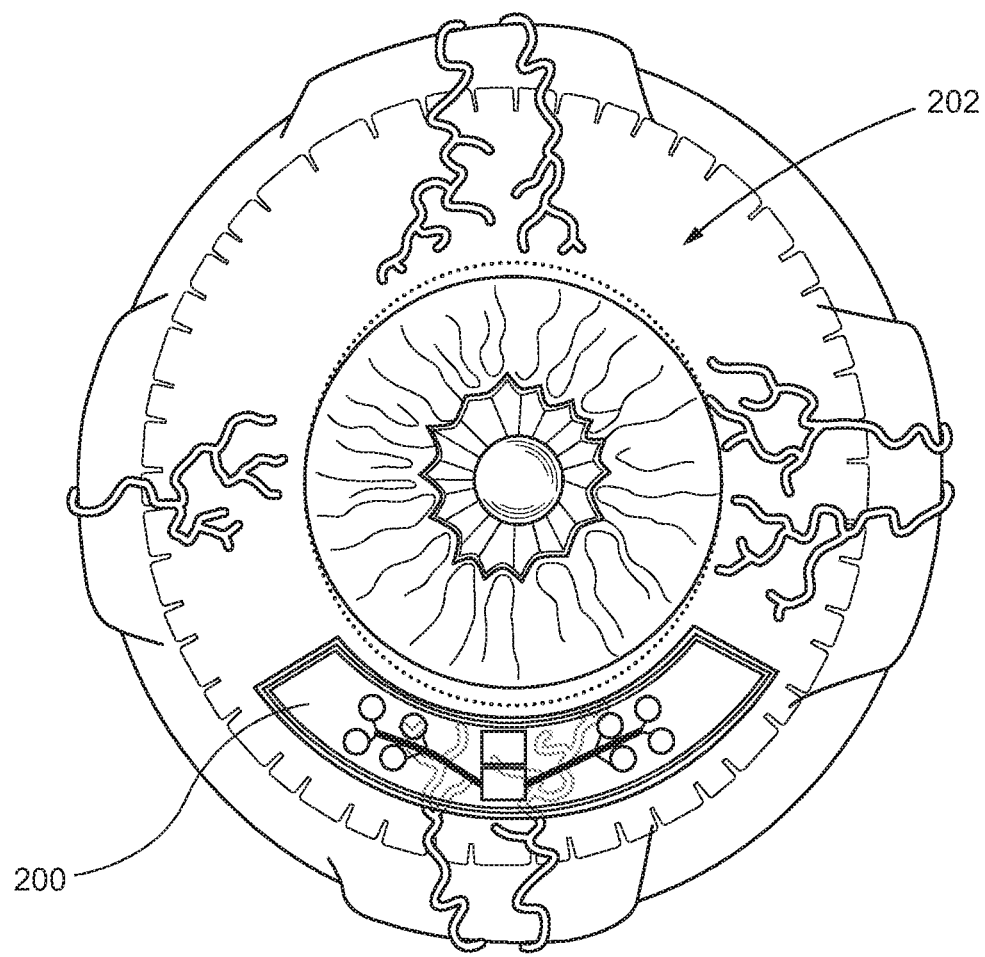
FIGS. 2A-2E show a sclera therapeutic agent release device in accordance with various embodiments.

In various embodiments, an eye mountable subtarsal (under eyelid) medical device is provided for customized on-demand scleral therapeutic agent release. FIG. 2A shows placement of an eye-mountable subtarsal device 200 for scleral therapeutic agent release on an eye 202. The device 200 is designed to fit discreetly under the eyelid leaving the corneal surface exposed and untouched. In some embodiments, the device 200 may be placed under the lower eyelid such that it is hidden at all times throughout the day while maintaining preferential contact to the scleral region beyond the corneoscleral junction or limbus for therapeutic agent release. The device 200 may be worn continuously as episcleral localization is a low risk area for neovascularization compared to standard contact lenses where risk of corneal hypoxia exists. Moreover, the subtarsal placement of the therapeutic agent delivery devices or systems on the sclera is preferable for posterior segment treatment therapies over other treatment sites such as the cornea because the sclera is permeable to high molecular weight molecules that are common in therapeutic agents (e.g., molecules up to approximately 70 kDa), whereas the cornea is only permeable to molecules less than 1 kDa, thus restricting transcorneal therapy options available for the posterior segment. The posterior segment or posterior cavity is the back two-thirds of the eye that includes the anterior hyaloid membrane and all of the optical structures behind it including: the vitreous humor, retina, choroid, and optic nerve.

For surface released therapeutic agents, the lens-iris diaphragm is the main physical barrier to reaching the posterior tissues of the eye, so bypassing this barrier via the sclera is preferred. In addition, the sclera provides a large surface area of about 17 $cm^2$, comprising 95% of the surface area of the human eye. This large area provides abundant space for transscleral therapeutic agent absorption and allows delivery of neuroprotective agents, antioxidants, angiostatic agents and anti-vascular endothelial growth factor (VEGF) treatments to specific regions of the retina. Examples of posterior segment diseases where this type of device is of therapeutic benefit include, but are not limited to, macular degeneration, diabetic retinopathy, retinitis pigmentosa, retinal vein occlusions, sickle cell retinopathy, glaucoma, choroidal neovascularization, retinal neovascularization, retinal edema, retinal ischemia, and proliferative vitreoretinopathy.

Figure 2B:
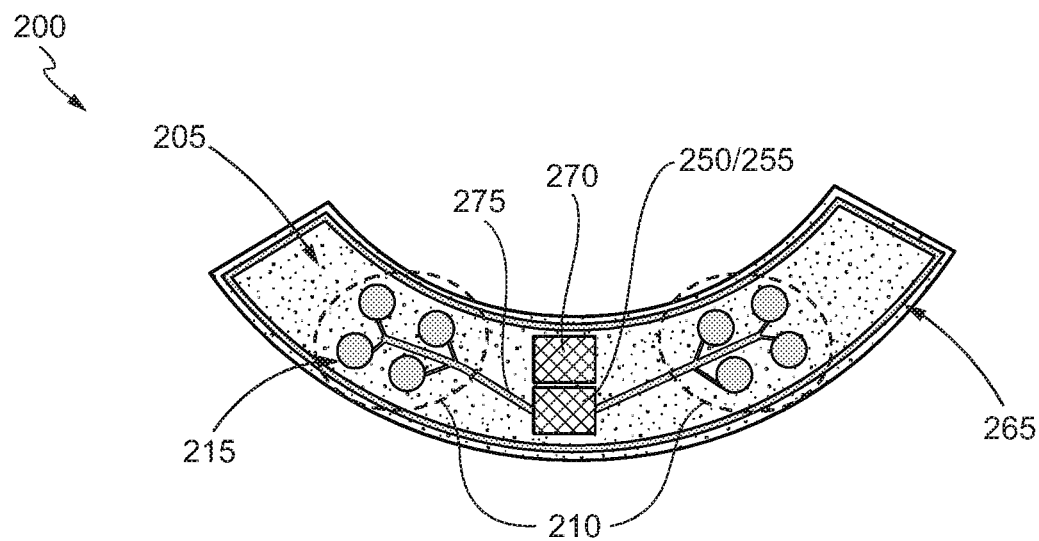

FIG. 2B shows the device 200 for scleral therapeutic agent release in accordance with various embodiments. The device 200 includes a polymeric substrate 205 comprising a release region(s) 210 comprising one or more reservoirs 215. The polymeric substrate 205 may be formed of polyimide, liquid crystal polymer, parylene, polyether ether ketone, polyethylene terephthalate, poly(methyl methacrylate), polyurethane, rigid gas permeable fluorosilicone acrylate, a silicon-based polymer, a silicone acrylate, cyclic olefin co-polymer (COP/COC), a hydrogel, or a combination thereof. In some embodiments, the polymeric substrate 205 has an average thickness (a thickness along an entire length of the device) between 0.01 mm and 2 mm, for example about 1 mm. In some embodiments, the therapeutic agent delivery device 200 has an average thickness (a thickness along an entire length of the device) between 0.01 mm and 3 mm, for example about 1.5 mm. The polymeric substrate 205 has a shape and sufficient flexibility for mounting to the contour of the tissue such as the eye. In certain embodiments, the shape is a semi-circle shape as shown in FIG. 2A. The flexibility of the polymeric substrate 205 may be characterized based on the flexural strength or flexural modulus of the polymer layer making up the polymeric substrate 205. The flexural strength of a material is its ability to resist deformation under load. For materials that deform significantly (sufficient flexibility) but do not break, the load at yield, typically measured at 5% deformation/strain of the outer surface, is reported as the flexural strength or flexural yield strength. In certain embodiments, the polymeric substrate 205 has a flexural strength or flexural yield strength of between 30 MPa and 175 MPa, preferably between 40 MPa and 130 MPa, for example about 100 MPa, and has a flexural modulus between 0.5 and 7.5 GPa, preferably between 1.0 GPa and 5.0 GPa, for example about 3 GPa, which is measured using a ASTM D70 or ISO 178 test.

Figure 2C:
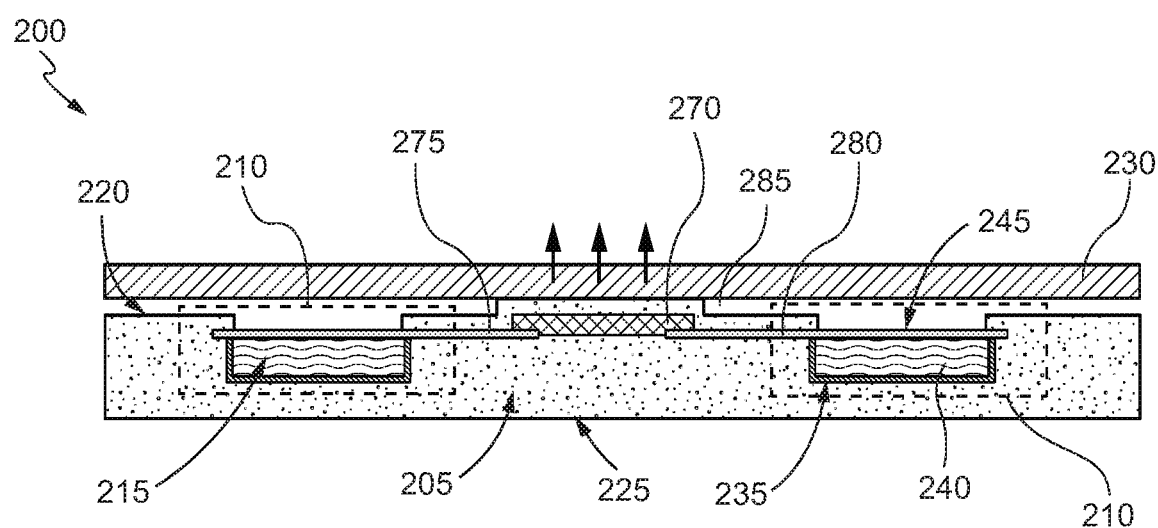

FIG. 2C shows a cross-section of the device 200 with two of the one or more reservoirs 215. In some embodiments, the polymeric substrate 205 comprises a distal surface 220 and a proximal surface 225 with one or more layers of polymer disposed therebetween. As used herein, the term "proximal surface" refers to a first surface of the substrate, while the term "distal surface" refers to a second surface opposing the first surface. For example, the distal surface 220 may be in contact with a surface of the tissue 230 (posterior), and the proximal surface 225 may be exposed from or not in contact with the surface of the tissue 230 (anterior). In some embodiments, therapeutic agent release is preferentially targeted on the scleral or tissue contacting surface therefore no agent is wasted to the proximal surface 225 or anterior side where agent can be lost to tear efflux and drainage. This results in greater efficacy while eliminating unintended systemic side effects.

In various embodiments, the one or more reservoirs 215 are integrated with or formed within the one or more layers of the polymer. The one or more reservoirs 215 may comprise a holding chamber 235 for a therapeutic agent 240 and an egress 245 for release of the therapeutic agent 240 from the holding chamber 235. The one or more reservoirs 215 are compatible with various physical forms of therapeutic agents including aqueous (liquid), gel, dry (powder), or other combinations thereof. In some embodiments, the one or more reservoirs 215 provide a means for temporary storage of one or more types of therapeutic agents 240 to allow for on-demand release and delivery of the therapeutic agents at a programmed time with a controlled rate thereby providing a therapeutic effect on the eye via transscleral absorption. In some embodiments, each reservoir 215 holds a single type of therapeutic agent 240 (same or different from other reservoirs). In other embodiments, each reservoir 215 holds multiple types of therapeutic agents 240 (same or different from other reservoirs). In other embodiments, a first type of therapeutic agent 240 is disposed within a first subset of the plurality of reservoirs 215 and a second type of therapeutic agent 240 is disposed within a second subset of the plurality of reservoirs 215. The one or more reservoirs 215 may have a volume from 0.01 nL to 100 µL, for example from 0.01 nL to 10 µL or about 1.0 µL, and stores a known quantity or volume of therapeutic agent. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. The one or more reservoirs 215 may be lined with a passive, hermetic, insulator, and/or inert coating such as a dielectric (e.g., $SiO_2$, $Al_2O_3$), or other approved agent-contacting material.

As shown in FIGS. 2B and 2C, the device 200 may further include a power source 250, a capacitor 255, a communications device 265 (e.g., a WiFi antenna), and an electronics module 270 (i.e., hardware, software or a combination thereof). In some embodiments, the power source 250, the capacitor 255, the communications device 265, and the electronics module 270 are integrated with or formed within the one or more layers of the polymer. In other embodiments, the power source 250, the capacitor 255, the communications device 265, and the electronics module 270 are formed on a top surface of the one or more layers of the polymer, e.g., formed on the proximal surface 225. In other embodiments, the power source 250, the capacitor 255, the communications device 265, and the electronics module 270 are formed on a separate polymeric substrate integrated with the substrate 205. In yet other embodiments, the power source 250, the capacitor 255, the communications device 265, and the electronics module 270 are formed within a housing integrated with the substrate 205 and/or a separate substrate. The housing may be comprised of materials that are biocompatible such as polymers, bioceramics or bioglasses for radio frequency transparency, or metals such as titanium.

The power source 250 may be connected (e.g., electrically connected) to the electronics module 270 to power and operate the components of the electronics module 270. The power source 250 may be connected (e.g., electrically connected) to the capacitor 255 to power and provide current flow for one or more circuits 275. The communications device 265 may be connected (e.g., electrically connected) to the electronics module 270 for wired or wireless communication with external devices via, for example, radiofrequency (RF) telemetry or WiFi. The electronics module 270 may be connected (e.g., electrically connected) to the capacitor 255 and the one or more circuits 275 such that the electronics module 270 is able to apply a signal or electrical current to electronic components such as gates, electrodes, or sensors connected to the one or more circuits 275. The electronics module 270 may include discrete and/or integrated electronic circuit components (e.g., one or more processors) that implement analog and/or digital circuits capable of producing the functions attributed to the device 200 such as applying a potential to a controlled release mechanism, applying a potential to a circuit, or applying a potential to one or more electrodes. In various embodiments, the electronics module 270 may include software and/or electronic circuit components such as a signal generator that generates a signal causing the capacitor 255 or the one or more circuits 275 to deliver a voltage, potential, current, optical signal, or ultrasonic signal to electronic components, a controller that determines or senses signals either received from external devices via the communications device 265 or via electrodes or sensors connected to the one or more circuits 275, controls release and delivery parameters of the device 200, and/or causes release and delivery of the therapeutic agent 240 via the one or more reservoirs 215, and a memory with program instructions operable on by the signal generator and the controller to perform one or more processes for releasing or delivering the therapeutic agents 240.

In various embodiments, the device 200 achieves release of the therapeutic agent 240 from the one or more reservoirs 215 to the tissue 230 via an active, passive, or combination thereof controlled release mechanism 280 (see, e.g., FIG. 2C). In some embodiments, the one or more reservoirs 215 comprises the holding chamber 235 for the therapeutic agent 240, the egress 245, and the active, passive, or combination thereof controlled release mechanism 280 that temporarily blocks passage of the therapeutic agent 240 from the holding chamber 235 through the egress 245. In some embodiments, a single controlled release mechanism 280 is provided for each of the one or more reservoirs (same or different mechanism provide for each reservoir). In other embodiments, a plurality of controlled release mechanism 280 are provided for each of the one or more reservoirs (same or different mechanisms provide for each reservoir). In other embodiments, a single controlled release mechanism 280 is provided for some of the one or more reservoirs, while a plurality of controlled release mechanism 280 are provided for others of the one or more reservoirs (same or different mechanism(s) provide for each reservoir). While the arrangement of the control release mechanism, reservoirs, and therapeutic agents are described herein in particular detail with respect to several described embodiments, it should be understood that other arrangements have been contemplated without departing from the spirit and scope of the present invention. For example, different arrangements of the control release mechanism, reservoirs, and therapeutic agents are contemplated herein such that the release and delivery of a therapeutic agent(s) is targeted both temporally and spatially to a surface of the tissue (e.g., the scleral surface of the eye) where optimal therapeutic agent transfer into the tissue may occur.

In some embodiments, the controlled release mechanism 280 is passive. As used herein, "passive" means that an external stimulus is not being applied to cause the opening/closing of the mechanism for release of the therapeutic agent. In certain embodiments, the controlled release mechanism 280 is a passive polymer device (or device constructed of a similar material). For example, a passive polymer device may be used as a part of the control release mechanism to provide controlled release of the therapeutic agent 240 in constant doses over long periods, cyclic dosage, and tunable release of both hydrophilic and hydrophobic therapeutic agents. The polymer device may be a diffusion-controlled (membrane or monolithic controlled) device, a degradable-controlled (erosion or chemically controlled) device, or a solvent-activated-controlled (swelling- or osmotically-controlled) device In a reservoir type diffusion-controlled device, the therapeutic agent may be encapsulated or provided behind a polymer membrane (e.g., encapsulated or closed off within the reservoir by a polymer layer). Diffusion through the polymer membrane is the rate limiting step. The polymer membrane may be formed of silicone ethylene-vinyl acetate copolymers, polyurethane, polyethylene, polymethylmethacrylate, polyhydroxyethylmethacrylate, a silicon-based polymer, a silicone elastomer, or a combination thereof. In a monolithic type diffusion-controlled device, the therapeutic agent may be distributed in a polymer matrix. For example, the therapeutic agent may be dissolved (or dispersed if the concentration exceeds the polymer's solubility limit) in a nonswellable or fully swollen matrix that does not degrade during its therapeutic life. Diffusion through the polymer membrane is the rate limiting step. Moreover, an environmental fluid such as tear film may leach the therapeutic agent out of the matrix if the polymer is permeable to the fluid. If a soluble additive is mixed in the polymer matrix, fluid may enter the matrix by dissolving the additive and forming interconnected channels for release of the therapeutic agent. The polymer matrix may be formed of polymethylmethacrylate, polyhydroxyethylmethacrylate, a hydrogel, a silicon-based polymer, a silicone elastomer, or a combination thereof.

In a degradable-controlled device, the therapeutic agent may be encapsulated or provided behind a polymer membrane or physically immobilized in the polymer and only released by erosion of the polymer (e.g., biodegradation or chemical degradation of the polymer). This type of device may be constructed as a reservoir type device or a monolithic type device. Degradation of the polymer membrane is the rate limiting step. Moreover, a chemical (e.g., an agent that causes degradation of the polymer) may be bound to the polymer, and release/activation of the chemical from the polymer, e.g., hydrolytic or enzymatic cleavage of a bond (e.g., by constituents in the tear film) may ultimately cause degradation of the polymer. The degradable polymer may be formed of poly-(vinyl pyrrolidone), partially esterified copolymers of methyl vinyl ether and maleic anhydride, copolymers of lactic and glycolic acid, polyanhydrides, or a combination thereof.

In a swelling-controlled device, the therapeutic agent may be dispersed or dissolved in a polymer matrix in which it is unable to diffuse to any significant extent. When the polymer matrix is placed in an environmental fluid (e.g., tear film) that is thermodynamically compatible with the polymer, the fluid is absorbed into the polymer causing it to swell. The therapeutic agent in the swollen part can then diffuse out of the device. The swellable polymer may be formed of a hydrogel, acrylamide, poly-(ethylene glycols), or a combination thereof. In a osmotic-controlled device, the therapeutic agent is released from being encapsulated or behind semi-permeable membrane with at least one egress or orifice by utilizing osmotic pressure as the driving force. In an aqueous environment (e.g., contact with a tear film), a fluid such as water is transported into the encapsulation or behind the semipermeable membrane by permeation. A non-extendible polymer facilitates the build-up of hydrostatic pressure, and a solution of the therapeutic agent and the fluid is pumped out of the egress or orifice. The non-extendible polymer may be formed of polymethylmethacrylate, polyhydroxyethylmethacrylate, a hydrogel, a silicon-based polymer, a silicone elastomer, or a combination thereof.

In some embodiments, the controlled release mechanism 280 is active. As used herein, "active" means that an external stimulus is being applied to cause the opening/closing of the mechanism for release of the therapeutic agent. For example, the device 200 may achieve on-demand drug release through electronic control of at least one valve (controlled release mechanism 280) that is physically coupled to the one or more reservoir 215 within the device 200. In certain embodiments, a circuit (e.g., one or more circuits 275) is formed on the polymeric substrate 205, and the circuit comprises a current source (e.g., the power source 250 and the capacitor 255) and at least one valve (the controlled release mechanism 280) such that a stimulus may be applied to open/close the at least one valve. A single reservoir may contain several "valves" which can be activated at selected times to increase the effective surface area available for diffusion to the scleral surface. This increases the effective dose provided at a given time. Alternatively, valves may be activated over time thereby maintaining a constant effective therapeutic dosage level over time. Alternatively, multiple discrete reservoirs with valves may be implemented, each with a discrete volume of drug for discretized bolus delivery.

The valves may be single use and opened on-demand electronically to allow therapeutic agent within the reservoir to pass through the valve opening towards the tissue, e.g., the scleral surface. Alternatively, the valves may be multi-use and opened/closed on-demand electronically to allow therapeutic agent within the reservoir to pass through the valve opening towards the tissue, e.g., the scleral surface. The valve opening action initiates therapeutic agent release into the thin post-device tear film located between the device and the sclera. The distance between the valve opening and the sclera is filled by the tear film (<20 μm), providing a short distance for a therapeutic agent to diffuse to the scleral surface. The combination of a thin tear film, subtarsal device placement and preferential therapeutic agent release to the scleral surface provides a quasi-static environment that promotes an increased therapeutic agent residence time (>30 minutes vs ~30 seconds for topical administration) and greater availability of therapeutic agent at the scleral surface, thus maximizing transscleral absorption and posterior segment bioavailability.

In certain embodiments, the controlled release mechanism 280 is an active polymer device (or device constructed of a similar material). For example, an active polymer device may be used as a part of the control release mechanism to provide controlled release of the therapeutic agent 240 in constant doses over long periods, in accordance with first-order constant release profiles, or in accordance with on-demand pulsatile signals/commands. In some embodiments, the therapeutic agent may be encapsulated or provided behind a polymer membrane (e.g., encapsulated or closed off within the reservoir by a polymer layer that acts as a valve). The polymer membrane may be an environmentally-controlled device with the ability to undergo a physical or chemical behavioral change in response to an external stimulus. For example, a temperature or pH change may be used to trigger the behavioral change of the polymer but other stimuli, such as ultrasound, ionic strength, redox potential, electromagnetic radiation, and chemical or biochemical agents, may be used. Types of behavioral change can include transitions in solubility, hydrophilic-hydrophobic balance, and conformation. Upon receiving the stimuli and undergoing the behavior change, the environmentally-controlled device may release the therapeutic agent from the reservoir(s). The polymer for the environmentally-controlled device may include hydrogels, micelles, polyplexes, polymer-drug conjugates, or combinations thereof. Hydrogels are hydrophilic (co)polymeric networks capable of imbibing large amounts of water or biological fluids. Physical or covalent crosslinks may render hydrogels insoluble in water. Various hydrogels can be engineered in accordance with aspects of the present invention to respond to numerous stimuli.

In certain embodiments, the controlled release mechanism 280 is an active metal device (or device constructed of a similar material). For example, an active metal device may be used as a part of the control release mechanism to provide controlled release of the therapeutic agent 240 in constant doses over long periods, in accordance with first-order constant release profiles, or in accordance with on-demand pulsatile signals/commands. In some embodiments, the therapeutic agent may be encapsulated or provided behind a metallic film (e.g., encapsulated or closed off within the reservoir by a metal layer that acts as a valve). Therapeutic agent release may be activated electronically through application of a potential or low-level voltage stimulus to a metallic thin film comprising the valve. In some embodiments, the thin film forms a seal on a side of the reservoir, which may be positioned against the tissue (see, e.g., FIG. 2C). The metallic film undergoes electrodissolution when a potential is applied under presence of the environmental fluid 285 (e.g., a tear film). The release mechanism may be described through the following equilibrium equations (1) $Au + 2Cl^- \leftrightarrows (AuCl_2^-)ads + e$ and (2) $(AuCl_2^-)ads \rightarrow AuCl_2^-$ (soln) with the rate limiting step being the activated desorption of the gold complex from the surface.

In some embodiments, gold is used as the metal film material because it is easily deposited and patterned, has a low reactivity with other substances and resists spontaneous corrosion in many solutions over the entire pH range. Gold has also been shown to be a biocompatible material. However, the presence of a small amount of chloride ion, as is naturally found in tear fluid, creates an electric potential region which favors the formation of soluble gold chloride complexes. Holding the anode potential in this corrosion region between 0.8 and 1.2 V, for example at about 1.0 V, enables reproducible gold dissolution of films having a thickness of between about 50 nm and about 500 nm. Potentials below this region are too low to cause appreciable corrosion, whereas potentials above this region result in gas evolution and formation of a passivating gold oxide layer that causes corrosion to slow or stop. Other metals such as copper or titanium tend to dissolve spontaneously under these conditions or do not form soluble materials on application of an electric potential. Although gold is used in some embodiments, it should understood that other materials may be used to achieve similar electrodissolution-mediated agent release.

In some embodiments, the controlled release mechanism 280 is a combination of one or more passive devices and one or more active devices. In certain embodiments, the controlled release mechanism 280 is a passive polymer device (or device constructed of a similar material) and an active polymer or metal device. For example, an active polymer or metal device may be used as a part of the control release mechanism to provide controlled release of the therapeutic agent 240 from the one or more reservoirs 215. The therapeutic agent 240 may be encapsulated or provided behind a polymeric or metallic layer (e.g., encapsulated or closed off within the reservoir by a polymeric or metallic layer that acts as a valve). Once the active polymer or metal device is opened via external stimulus, the therapeutic agent 240 may be released out of the holding chamber 235 through the egress 245 into a passive polymer device such a polymeric matrix or hydrogel. Once the therapeutic agent 240 passes through the passive polymer device (e.g., via diffusion or osmotic pump), the therapeutic agent 240 may be released and delivered to a surface of a target tissue 230 (e.g., the scleral surface). Alternatively, a passive polymer device may be used as a part of the control release mechanism to provide controlled release of the therapeutic agent 240 from the one or more reservoirs 215. The therapeutic agent 240 may be encapsulated or provided behind a polymeric layer (e.g., encapsulated or closed off within the reservoir by a polymeric layer that acts as a valve). Once the therapeutic agent 240 passes through the passive polymer device (e.g., via diffusion or osmotic pump), the therapeutic agent 240 may be released out of the holding chamber 235 through the egress 245 into an active polymer or metal device such as encapsulated or provided behind a polymeric or metallic layer. Once the active polymer or metal device is opened via external stimulus, the therapeutic agent 240 may be released and delivered to a surface of a target tissue 230 (e.g., the scleral surface)

Figure 2D:
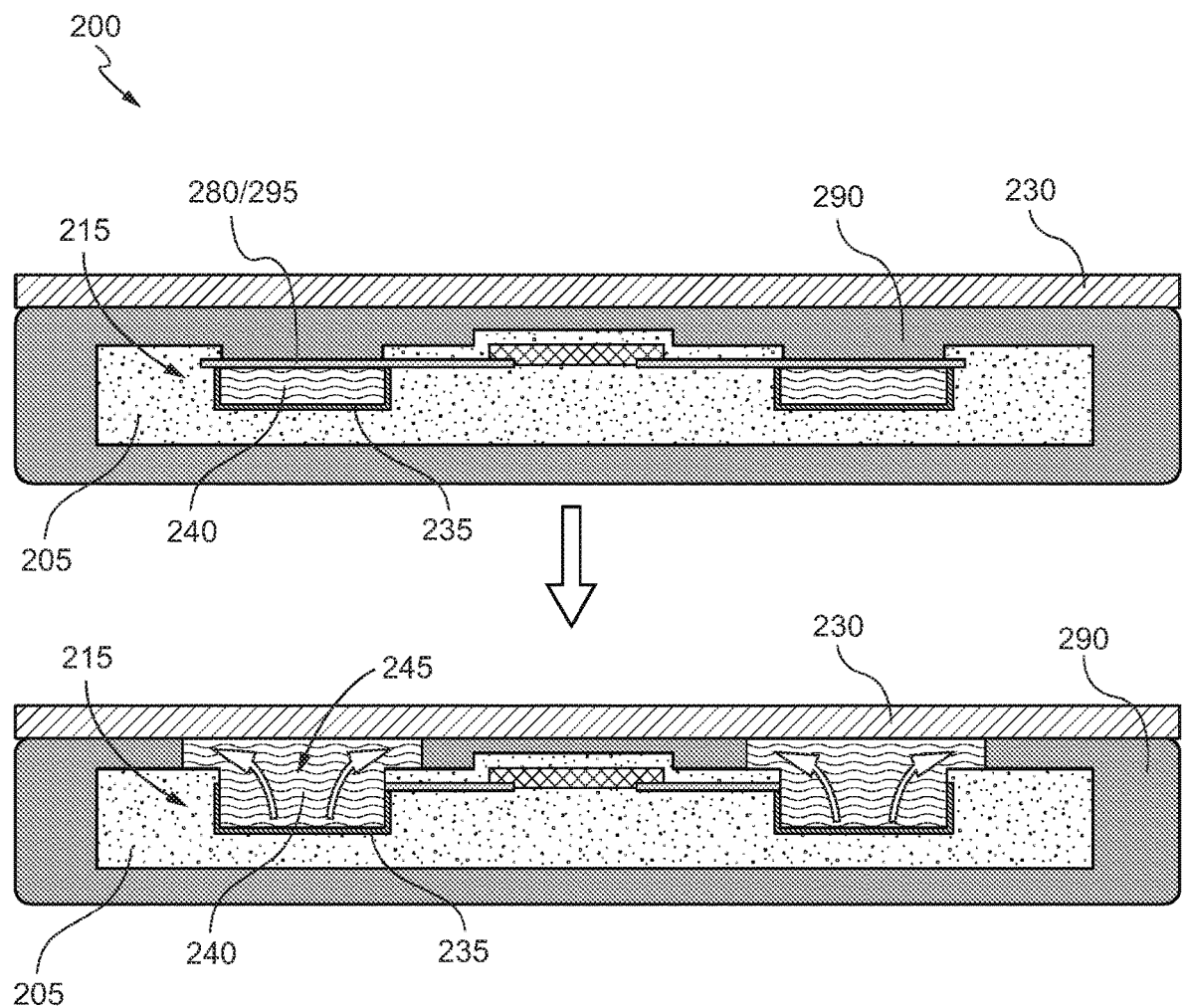
Figure 2E:
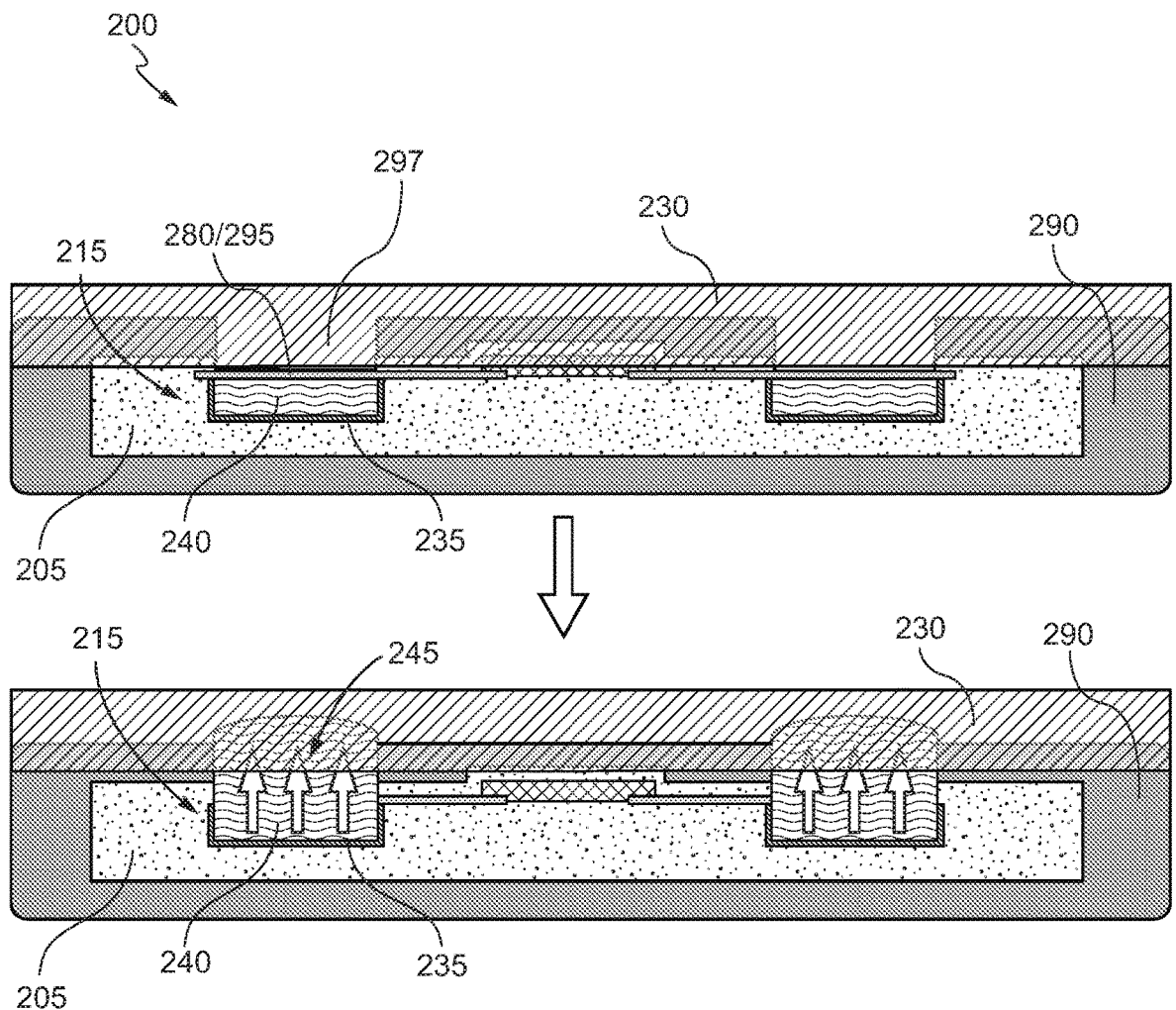

As shown in FIGS. 2D and 2E, the device 200 may further include an overmold polymeric layer 290 formed around substantially an entirety of the polymeric substrate 205. In some embodiments, the polymeric substrate 205 is fully encapsulated by the overmold polymeric layer 290 (see, e.g., FIG. 2D). The overmold polymeric layer 290 may be formed of polymethylmethacrylate, polyhydroxyethylmethacrylate, a hydrogel, a silicon-based polymer, a silicone elastomer, or a combination thereof. In certain embodiments, the overmold polymeric layer 290 has a water content between 30% and 50%, for example about 45% water content. In some embodiments, the controlled release mechanism 280 is a combination of a metallic thin film 295 and the overmold polymer layer 290 (a polymeric passive device). The therapeutic agent 240 may be encapsulated or provided behind the metallic thin film 295 (e.g., encapsulated or closed off within the reservoir by a metallic layer that acts as a valve). Once the metallic thin film 295 is opened via external stimulus and dissolution, the therapeutic agent 240 may be released out of the holding chamber 235 of the reservoir 215 through the egress 245 into the overmold polymeric layer, as shown in FIG. 2D. Once the therapeutic agent 240 passes through the passive polymer device (e.g., via diffusion or osmotic pump), the therapeutic agent 240 may be released and delivered to a surface of a target tissue 230 (e.g., the scleral surface). This mechanism for release of the therapeutic agent may be used to achieve agent release kinetics similar to passive load-and-release drug-eluting approaches albeit with a fully-programmable and customizable active release initiation.

In other embodiments, the device 200 includes exposed access points or openings 297 in the overmold polymeric layer 290 (e.g., hydrogel), which exposes a surface of the one or more reservoirs 215 (see, e.g., FIG. 2E). In these embodiments, the post-device tear film or tissue 230 is in direct contact with the controlled release mechanism 280 or the egress 245 of the reservoir 215. The term "direct" or "directly", as used herein, may be defined as being without something in between. The term "indirect" or "indirectly", as used herein, may be defined as having something in between. Upon release of the therapeutic agent 240 from the chamber 235, the therapeutic agent 240 permeates directly into the post-device tear film or tissue 230. This mechanism for release may be used to achieve alternative release kinetics with fully-programmable and customizable active release similar to topical application of eye drops however with the benefit of drastically increased residence times, increased bioavailability and minimal drug loss. More generally, the device 200 enables customized delivery profiles which is currently unavailable with either topical eye drops or intravitreal needle injection. Advantageously, where the therapeutic window changes or is cyclic (e.g., due to circadian rhythm such as in glaucoma), the device 200 is able to meet these changes in a fully customized manner.

While various embodiments are disclosed herein with respect to an eye mountable subtarsal (under eyelid) therapeutic agent release device, this is not intended to be restrictive. In addition to providing for customized on-demand scleral therapeutic agent release, the teachings disclosed herein can also be applied to other therapeutic agent release devices for other tissues. For example, the therapeutic agent delivery device may be designed to fit discreetly over at least a portion of the corneal surface such that the device does not block or affect vision in any way and is compatible with standard contact lens materials while maintaining preferential contact to the cornea for therapeutic agent delivery to the anterior segment of the eye. The anterior segment or anterior cavity is the front third of the eye that includes the structures in front of the vitreous humour: the cornea, iris, ciliary body, and lens. Examples of anterior segment diseases where this type of device or system is of therapeutic benefit include, but are not limited to, keratitis, abrasion, corneal neovascularization, fuch's dystrophy, keratoconus, keratoconjunctivitis sicca, iritis, and uveitis.

Sclera Therapeutic Agent Release Device with Facilitated Delivery

Figure 3:
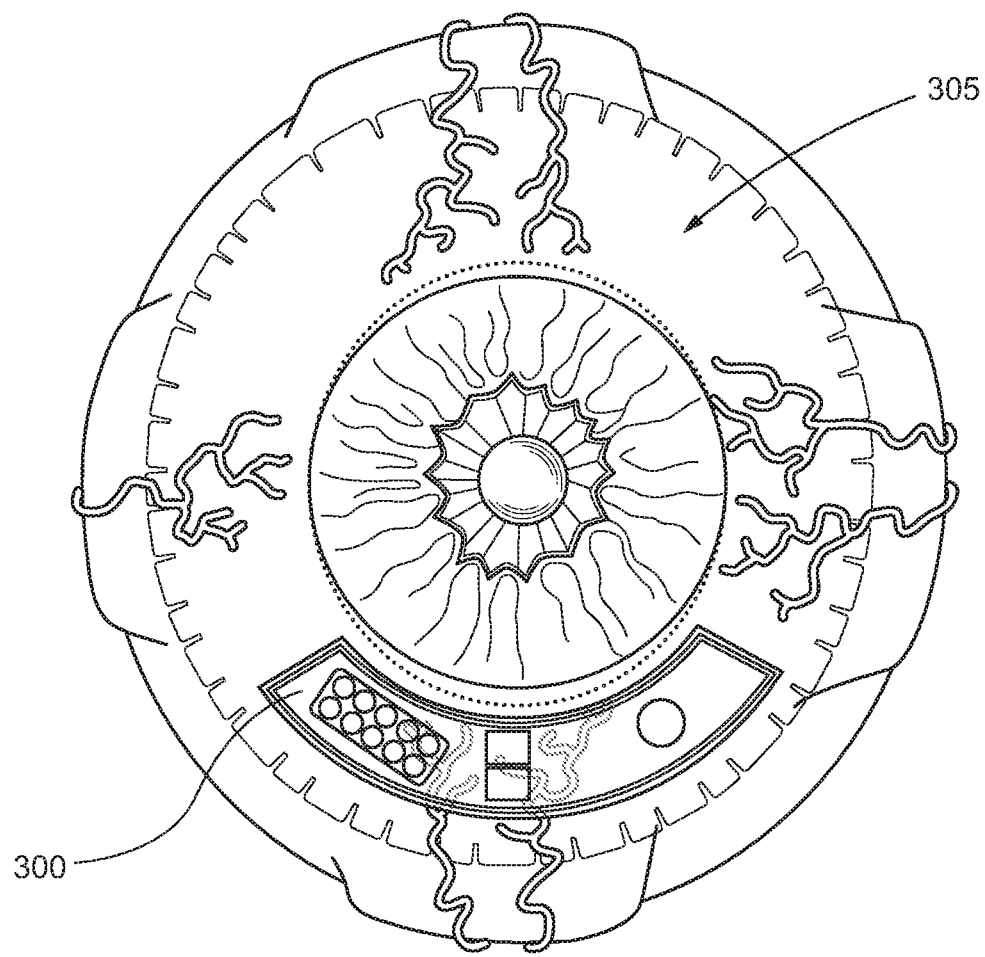
FIG. 3 shows subtarsal positioning of a sclera therapeutic agent release device with facilitated delivery in accordance with various embodiments.

In various embodiments, an eye mountable subtarsal (under eyelid) medical device is provided for customized on-demand iontophoretic therapeutic agent delivery. FIG. 3 shows placement of an eye-mountable subtarsal device 300 for scleral therapeutic agent release and delivery on an eye 305. The device 300 is designed to fit discreetly under the eyelid leaving the corneal surface exposed and untouched. In some embodiments, the device 300 may be placed under the lower eyelid such that it is hidden at all times throughout the day while maintaining preferential contact to the scleral region beyond the corneoscleral junction or limbus for therapeutic agent release. This large area provides abundant space for transscleral therapeutic agent absorption and allows delivery of neuroprotective agents, antioxidants, angiostatic agents and anti-vascular endothelial growth factor (VEGF) treatments to specific regions of the retina. Furthermore, drug penetration across the sclera can also be greatly increased beyond passive diffusion alone by means of an external energy source, in particular by iontophoresis. Examples of posterior segment diseases where this type of device is of therapeutic benefit include, but are not limited to, macular degeneration, diabetic retinopathy, retinitis pigmentosa, retinal vein occlusions, sickle cell retinopathy, glaucoma, choroidal neovascularization, retinal neovascularization, retinal edema, retinal ischemia, and proliferative vitreoretinopathy.

Figure 4:
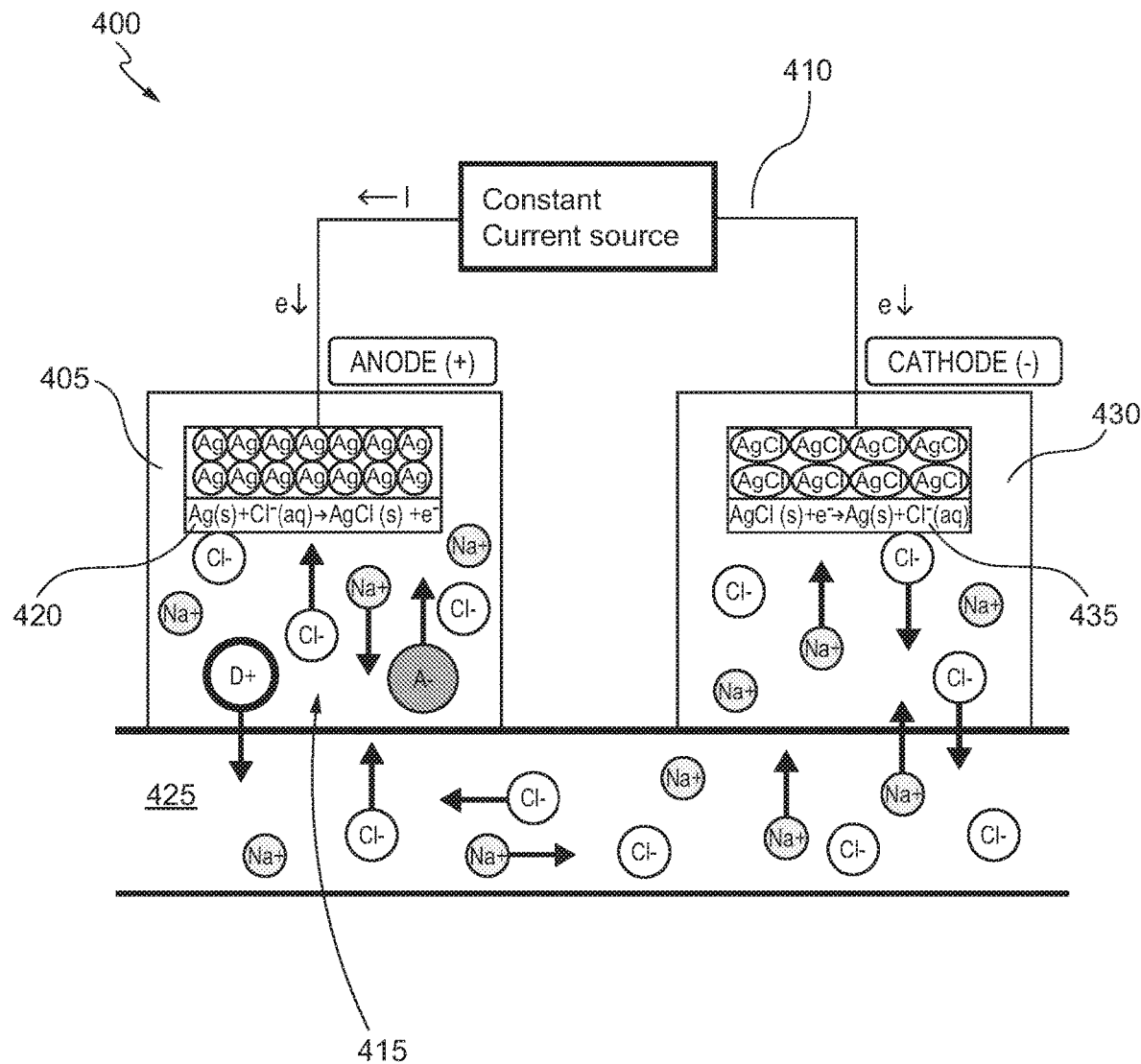
FIG. 4 shows an iontophoretic electrode system in accordance with various embodiments.

Iontophoresis is a local non-invasive technique in which an electric field is applied to enhance ionized therapeutic agent penetration into tissue. Current densities used for the electric field range between 0.5 mA/cm$^2$ and 50 mA/cm$^2$, for example about 5.0 mA/cm$^2$. The therapeutic agent may be applied with an electrode carrying the same charge as the therapeutic agent, and the ground electrode, which is of the opposite charge, is in contact with non-active species elsewhere to complete the circuit. The therapeutic agent serves as a conductor of the current through the tissue. As shown in FIG. 4, iontophoresis generally enhances therapeutic agent delivery by three mechanisms: electrophoresis, electroosmosis, and electroporation. Electrophoresis is the facilitation of the movement of ionic species by the applied electric field. Electroosmosis assists (or retards) the transport of both neutral and charged species by electric field-induced convective solvent flow. Electroporation describes barrier alteration that increases the intrinsic permeability of the membrane. The ionized substances are driven into the tissue by electrorepulsion at either the anode (for positive agent) or the cathode (for negatively charged agent). This ionic-electric field interaction, known as the Nernst-Planck effect is the largest contributor to flux enhancement for small ions, but not the only one. Electroosmotic flow is the bulk fluid flow which occurs when a voltage difference is imposed across a charged membrane. Since human membranes are negatively charged above pH 4, the electroosmotic flow occurs from anode to cathode, as the flow of the cationic counterions. For large monovalent ions the electroosmotic flow is the dominant flow mechanism.

In various embodiments, an electrode system 400 such as an Ag—Ag/Cl electrode system is used for its ability to maintain local pH levels and eliminate soluble bulk electrode species. However, the electrode system 400 may comprise other electrode materials such as platinum, platinum/iridium (PtIr) and alloys thereof, carbon, zinc/zinc chloride, gold, other suitable insoluble and inert metals that resist electrodissolution in solution over a given pH range, and combinations thereof. The anodal chamber 405 contains an ionizable agent D+ with its counter-ion A− and NaCl (tear film). Application of an electric potential causes a current to flow through the circuit 410. At the electrode solution interface 415, the Ag+ and Cl− react to form insoluble AgCl which is deposited on the electrode surface 420. Electromigration transports the cations, including the ionizable agent D+, from the anodal compartment 405 and into the tissue 425. At the same time, endogenous anions, primarily Cl−, move into the anodal compartment 405. In the cathodal chamber 430, Cl− ions are released from the electrode surface 435 and electroneutrality requires that either an anion is lost from the cathodal chamber 430 or that a cation enters the cathodal chamber 430 from the tissue 425. The extent and penetration depth of iontophoretic delivery is related to the electric field and the duration of application.

In some embodiments, electrode system 400 is a fully ambulatory wearable system with a combination of precision microelectrode geometry, low current density and long duration (e.g., hours-days), which facilitates therapeutic agent delivery paradigms that are not currently possible in tethered clinical settings. In certain embodiments, charge controlled iontophoresis (CCI) is used whereby the voltage is automatically modulated in accordance with changing tissue impedance in order to provide precise regulation of the current density and charge at the electrode interface. For example, application of 1 uA through a lithographically defined 100×100 μm anodic electrode produces a current density of 10 mA/cm2, a level shown to be safe and effective for scleral iontophoresis. In some embodiments, the electrode system 400 utilizes a single anode and single cathode to generate an appropriate electric field. In other embodiments, multiple microelectrodes (anodes and/or cathodes) are used to generate an appropriate electric field. The combination of a thin tear film, subtarsal device placement and preferential therapeutic agent release to the scleral surface provides a quasi-static environment that promotes an increased therapeutic agent residence time (>30 minutes vs ~30 seconds for topical administration) and greater availability of therapeutic agent at the scleral surface, thus maximizing transscleral absorption and posterior segment bioavailability.

The anode and cathode electrode placement on the substrate or device is also important as physical distance between electrodes affects iontophoretic delivery due to the anatomy of the eye which can yield different transscleral routes of penetration and barriers. According to the Nernst-Planck theory, the total flux of a molecule during iontophoresis is given by $J_{IONTO}=J_P+J_{EM}+J_{EO}$, where $J_P$ is the passive flux, $J_{EM}$ represents the electromigration (electrophoresis) contribution and $J_{EO}$ represents the electroosmotic contributions. For ions of appreciable charge, $$J_{EM} = D\frac{CzF}{RT}\frac{dE}{dx},$$

where D is the diffusion coefficient of the solute across the membrane, z is the solute charge, C is the concentration of the solute, F is the Faraday Constant, R is the gas constant and T is absolute temperature. For molecules that are substantially neutral, $J_{EM}$ is equal to zero and the $J_{EO}$ (uLcm$^{-2}$ h$^{-1}$), i.e. the current induced water flow across the tissue, is substantially equal to $J_{IONTO}$. Accordingly, in some embodiments, each of the plurality of cathode chambers and/or cathodes are spaced at least a predetermined distance from each of the plurality of anode chambers and/or anodes. In certain embodiments, the predetermined distance is greater than 1.0 mm, for example between 1.5 mm and 8 mm, or about 2.0 mm. The advantage of iontophoresis for ocular therapeutic agent delivery is that it safely provides high intraocular therapeutic agent tissue concentrations while minimizing the systemic drug exposure. The possibility of repeatedly delivering the therapeutic agent by this technique makes this treatment modality very useful for chronic and long-term intraocular diseases while minimizing risks associated with intravitreal injection including trauma (retinal detachment, endophthalmitis and globe perforation), infection, inflammation, and hemorrhage.

Figure 5:
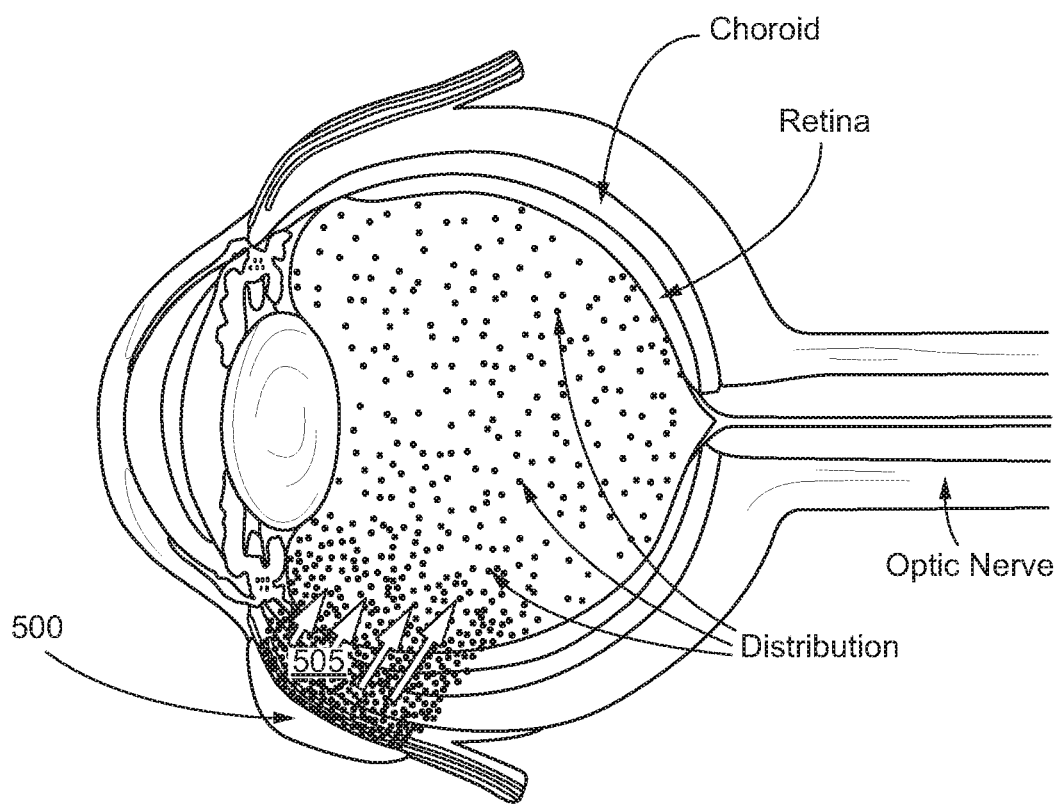
FIG. 5 shows a sclera therapeutic agent release device with facilitated delivery into the tissue of the eye in accordance with various embodiments.

FIG. 5 shows a device 500 for subtarsal iontophoretic therapeutic agent delivery in accordance with various embodiments. In some embodiments, the device 500 is ideally placed on the conjunctiva, over the pars-plana area to avoid current-based damage to the retina and minimize vascular absorption due to the thinner choroid in this region. As discussed with respect to FIGS. 2A-2D, a therapeutic agent may be released actively, that is, released on-demand electronically from the reservoir into a delivery region of the device where the therapeutic agent can be delivered iontophoretically 505. Additionally or alternatively, the therapeutic agent may be released passively, from a polymer-matrix or gel for example, and then delivered iontophoretically 505. A combination thereof including active and passive therapeutic agent release of one or more therapeutic agents may be executed by the device 500 and used in combination with active transscleral delivery via iontophoretic action 505.

Figure 6A:
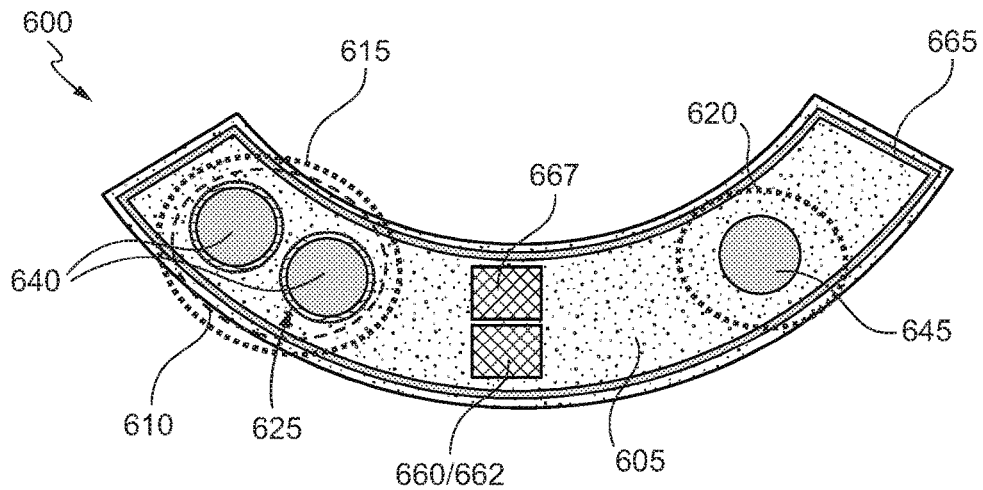
FIGS. 6A-6G show sclera therapeutic agent release device with facilitated delivery in accordance with various embodiments.

As shown in FIG. 6A, a therapeutic agent delivery device 600 (e.g., the subtarsal iontophoretic therapeutic agent delivery device discussed with respect to FIG. 5) may include a polymeric substrate 605 comprising a release region 610, a delivery region 615, and a receiving region 620. The release region 610 includes one or more areas of the device 600 that support the one or more reservoirs 625, the therapeutic agent 630 disposed within the one or more reservoirs 625, and an active, passive, or combination thereof controlled release mechanism 635 for release of the therapeutic agent 630 from the one or more reservoirs 625 into the delivery region 615. The delivery region 615 includes one or more areas of the device 600 that support a chamber or compartment (e.g., an anode chamber) that comprises a first iontophoresis electrode 640 (e.g., an anode) for transport of the therapeutic agent 630 from the delivery region 615 into a target tissue 632 (e.g., the vitreous humor) via electromigration. The receiving region 620 includes one or more areas of the device 600 that support a chamber or compartment (e.g., a cathode chamber) that comprises a second iontophoresis electrode 645 (e.g., a cathode) for maintaining electroneutrality within the tissue 632 (e.g., the sclera). As many of the features (e.g., the polymeric substrate 605, the release region 610, the one or more reservoirs 625, the therapeutic agent 630, the active, passive, or combination thereof controlled release mechanism 635) of device 600 are the same as the features described with respect to device 200 in FIGS. 2A-2D, the detailed description of such features is not repeated here for brevity, and instead this section focuses on the features (e.g., delivery region 615, the receiving region 620, the first iontophoresis electrode 640, and the second iontophoresis electrode 645) that provide an external energy source for delivery of the therapeutic agent 630 into the tissue 632.

Figure 6B:
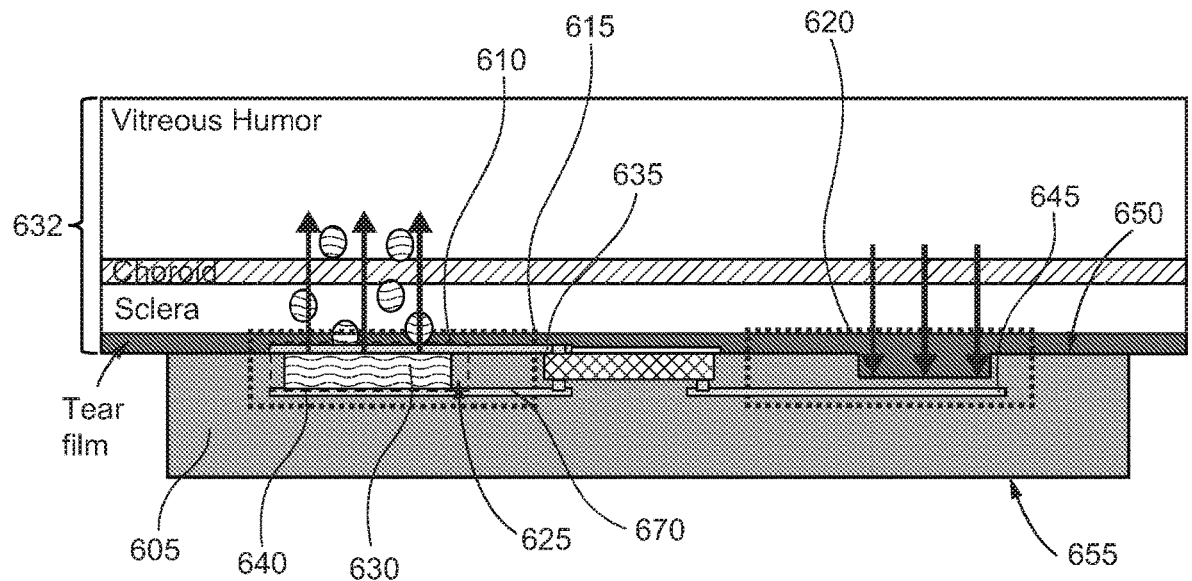

FIG. 6B shows a cross-section of the device 600 with the release region 610 and the delivery region 615 at least partially overlapping, or otherwise being co-located within the polymeric substrate 605. The receiving region 620 is disposed on an end of device 605 that is opposite the end having the delivery region 615. In some embodiments, the polymeric substrate 205 comprises a distal surface 650 and a proximal surface 655 with one or more layers of polymer disposed therebetween. For example, the distal surface 650 may be in contact with a surface of the tissue 632 (posterior), and the proximal surface 655 may be exposed from or not in contact with the surface of the tissue 632 (anterior). In some embodiments, therapeutic agent release is preferentially targeted on the scleral or tissue contacting surface therefore no agent is wasted to the proximal surface 655 or anterior side where agent can be lost to tear efflux and drainage. This results in greater efficacy while eliminating unintended systemic side effects.

In various embodiments, the one or more reservoirs 625 are integrated with or formed within the one or more layers of the polymer. The one or more reservoirs 625 may comprise a holding chamber for the therapeutic agent 630 and an egress for release of the therapeutic agent 630 from the holding chamber. The one or more reservoirs 625 are compatible with various physical forms of therapeutic agents including aqueous (liquid), gel, dry (powder), or other combinations thereof. In some embodiments, the one or more reservoirs 625 provide a means for temporary storage of one or more types of therapeutic agents to allow for on-demand release and delivery of the therapeutic agents at a programmed time with a controlled rate thereby providing a therapeutic effect on the eye via transscleral delivery. In some embodiments, each reservoir holds a single type of therapeutic agent (same or different from other reservoirs). In other embodiments, each reservoir holds multiple types of therapeutic agents (same or different from other reservoirs). The one or more reservoirs 625 may have a volume from 0.01 nL to 100 µL, for example from 0.01 nL to 10.0 µL or about 1.0 µL, and stores a known quantity or volume of therapeutic agent. The one or more reservoirs 625 may be lined with a passive, hermetic, insulator, and/or inert coating such as a dielectric (e.g., $SiO_2$, $Al_2O_3$), or other approved agent-contacting material.

As shown in FIGS. 6A and 6B, the device 600 may further include a power source 660, a capacitor 662, a communications device 665 (e.g., a WiFi antenna), and an electronics module 667 (i.e., hardware, software or a combination thereof). The power source 660 may be connected (e.g., electrically connected) to the electronics module 667 to power and operate the components of the electronics module 667. The power source 660 may be connected (e.g., electrically connected) to the capacitor 662 to power and provide current flow for one or more circuits 670. The communications device 665 may be connected (e.g., electrically connected) to the electronics module 667 for wired or wireless communication with external devices via, for example, radiofrequency (RF) telemetry or WiFi. The electronics module 667 may be connected (e.g., electrically connected) to the capacitor 662 and the one or more circuits 670 such that the electronics module 667 is able to apply a signal or electrical current to electronic components such as gates, electrodes, or sensors connected to the one or more circuits 670. In some embodiments, the one or more circuits 670 include a current source (e.g., the power source 660 and the capacitor 662), the first iontophoresis electrode 640 located within the delivery region 615 for transport of the therapeutic agent 630 from the delivery region 615 into a target tissue 632 via electromigration, and a second iontophoresis electrode 645 located within the receiving region 620 for maintaining electroneutrality within the tissue 632.

In various embodiments, the device 600 achieves release of the therapeutic agent 630 from the one or more reservoirs 625 to the delivery region 615 or an interface with the tissue 632 via the active, passive, or combination thereof controlled release mechanism 635 (see, e.g., FIG. 6B). In some embodiments, the one or more reservoirs 625 comprises the holding chamber for the therapeutic agent 630, the egress, and the active, passive, or combination thereof controlled release mechanism 635 that temporarily blocks passage of the therapeutic agent 630 from the holding chamber through the egress. In some embodiments, the controlled release mechanism 635 is a passive polymer device (or device constructed of a similar material). In some embodiments, the controlled release mechanism 635 is an active polymer device (or device constructed of a similar material). In some embodiments, the controlled release mechanism 635 is an active metal device (or device constructed of a similar material). In some embodiments, the controlled release mechanism 635 is a combination of one or more passive devices and one or more active devices. In some embodiments, the controlled release mechanism 635 is a passive polymer device (or device constructed of a similar material) and an active polymer or metal device.

In some embodiments, the release region 610 and the delivery region 615 are in fluidic communication. As used herein, "fluidic communication" means that a fluid such as the therapeutic agent is capable of flowing between the regions that are in communication or connected with one another. For example, once the therapeutic agent 630 is released from the one or more reservoirs 625 via the active, passive, or combination thereof controlled release mechanism 635, the therapeutic agent 630 is capable of flowing into the delivery region 615 or an interface with the tissue 632. In certain embodiments, at least a portion of the delivery region 615 is exposed to an environment external to the polymeric substrate 605. The external environment may be a tissue interface such as an interface between the polymeric substrate 605 and the tear film or scleral surface.

In some embodiments, one or more first electrode chambers such as an anode chamber is formed within the one or more layers of polymer (e.g., within a delivery region 615) and in fluidic communication with the one or more reservoirs 625. The one or more first electrode chamber comprises the first iontophoresis electrode 640. In certain embodiments, the first iontophoresis electrode 640 is located under the one or more reservoirs 625 formed within the release region 610 of the polymeric substrate 605. Moreover, at least a portion of the one or more first electrode chambers is exposed to an environment external to the polymeric substrate 605 at the distal surface 650. The one or more first electrode chambers are capable of receiving the therapeutic agent 630 from the reservoir upon release of the therapeutic agent 630 via the active, passive, or combination thereof controlled release mechanism 635. The therapeutic agent 630 may be ionizable, and a counter ion (the counter ion has a charge opposite that of the therapeutic agent 630) may be disposed within the one or more reservoirs 625 or the one or more first electrode chambers (e.g., within a delivery region 615). In embodiments in which multiple types of therapeutic agents are used, multiple types of counter ions may also be used (e.g., a first type of therapeutic agent may be ionized and a first type of counter ion has a charge opposite that of the first type of therapeutic agent and a second type of therapeutic agent may be ionized and the second type of counter ion has a charge opposite that of the second type of therapeutic agent. In some embodiments, a second electrode chamber such as cathode chamber is formed within the one or more layers of polymer (e.g., within a receiving region 620) and at least a portion of the second electrode chamber is exposed to an environment external to the polymeric substrate 605 at the distal surface 650. The second electrode chamber comprises the second iontophoresis electrode 645.

Figure 6C:
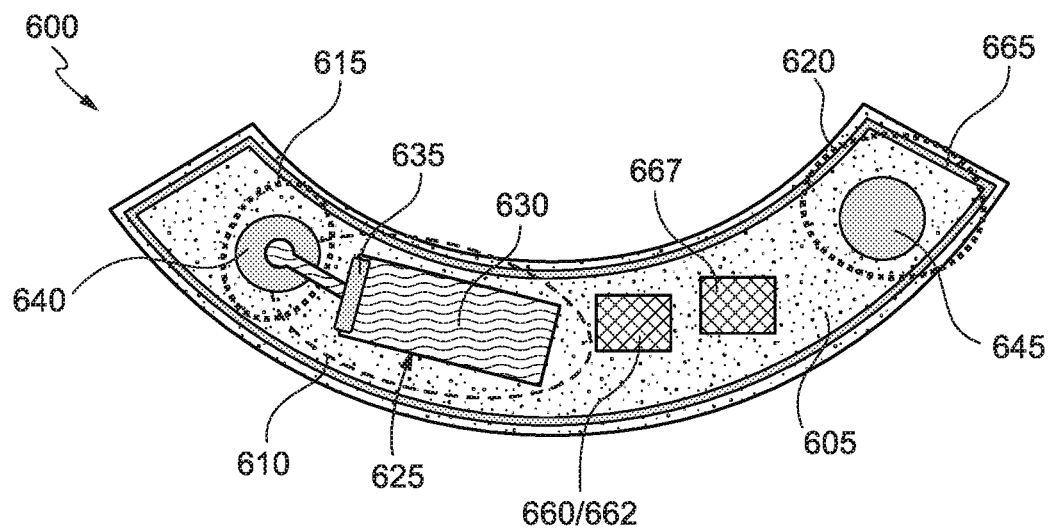

As shown in FIG. 6C, the device 600 may comprise a single reservoir 625 located separately from the iontophoretic delivery region 615. The reservoir 625 may release therapeutic agent 630 via the controlled release mechanism 635 into the iontophoretic delivery region 615 where the therapeutic agent 630 may be driven into the tissue 632. The delivery region 615 comprises a first electrode chamber having at least one first iontophoretic electrode 640 (e.g., a single anode electrode or multiple anode electrodes). Release from the reservoir 625 may be active, passive, or combination thereof. The receiving region 620 is located on an opposing end of the device 600 to ensure outward electromigration of the therapeutic agent 630 from the delivery region 615 into the tissue. The receiving region 620 comprises a second electrode chamber having at least one second iontophoretic electrode 645 (e.g., a single cathode electrode or multiple cathode electrodes).

Figure 6D:
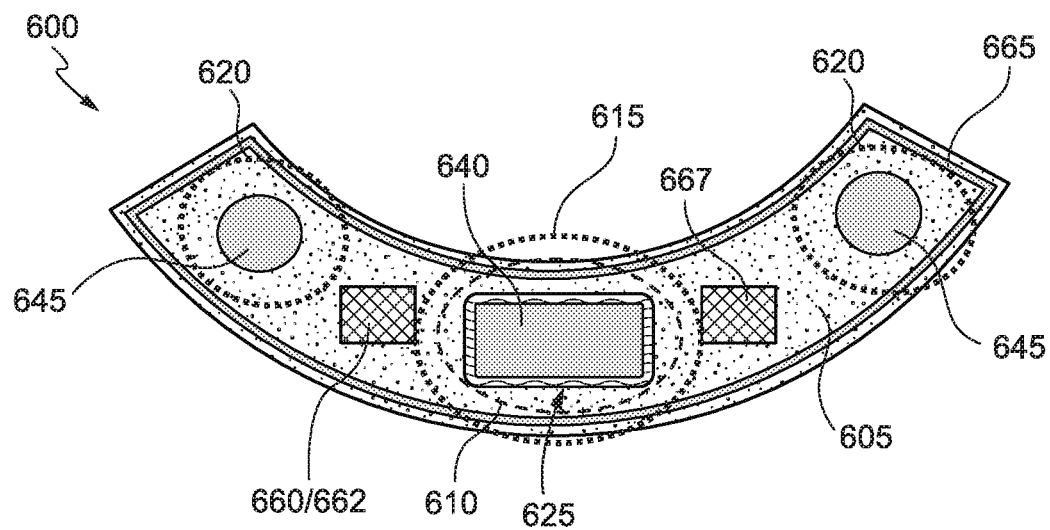
Figure 6E:
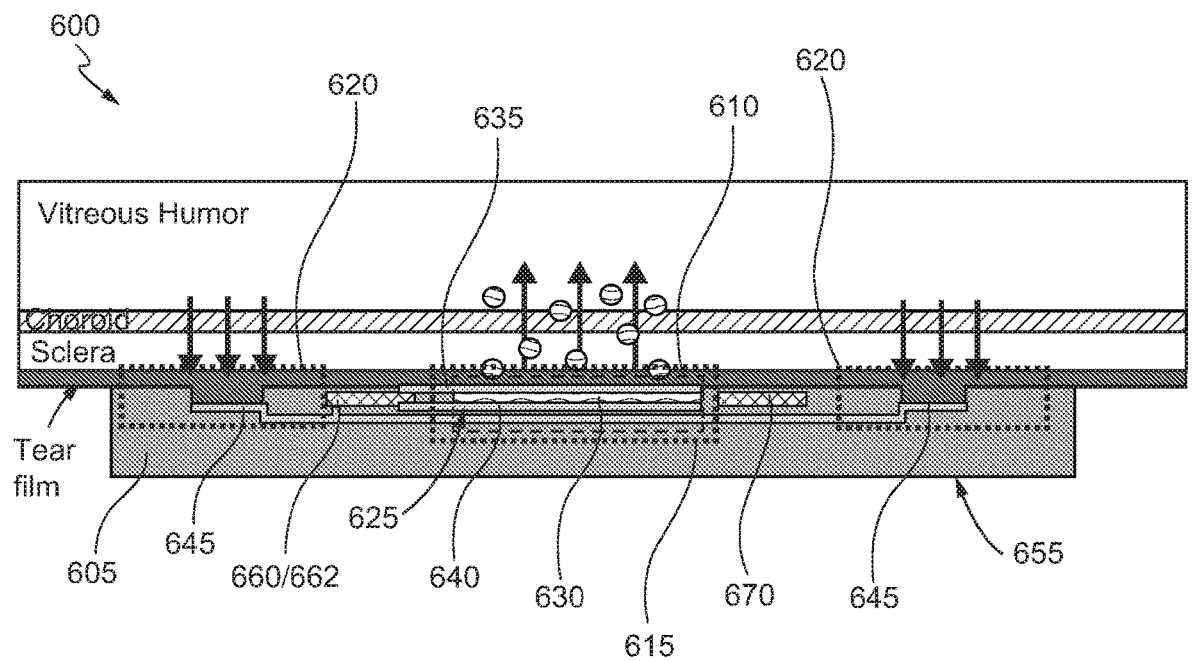

As shown in FIGS. 6D and 6E, the device 600 may comprise a single reservoir 625 located at a center of the device 600. The reservoir 625 may release therapeutic agent 630 via the controlled release mechanism 635 into the iontophoretic delivery region 615 where the therapeutic agent 630 may be driven into the tissue 632. The delivery region 615 is also located at a center of the device 600 and comprises a first electrode chamber having at least one first iontophoretic electrode 640 (e.g., a single anode electrode or multiple anode electrodes). Release from the reservoir 625 may be active, passive, or combination thereof. At least two receiving regions 620 are located on opposing ends of the device 600 to ensure outward electromigration of the therapeutic agent 630 from the delivery region 615 into the tissue. Each of the least two receiving regions 620 comprise a second electrode chamber having at least one second iontophoretic electrodes 645 (e.g., a single cathode electrode or multiple cathode electrodes).

Figure 6F:
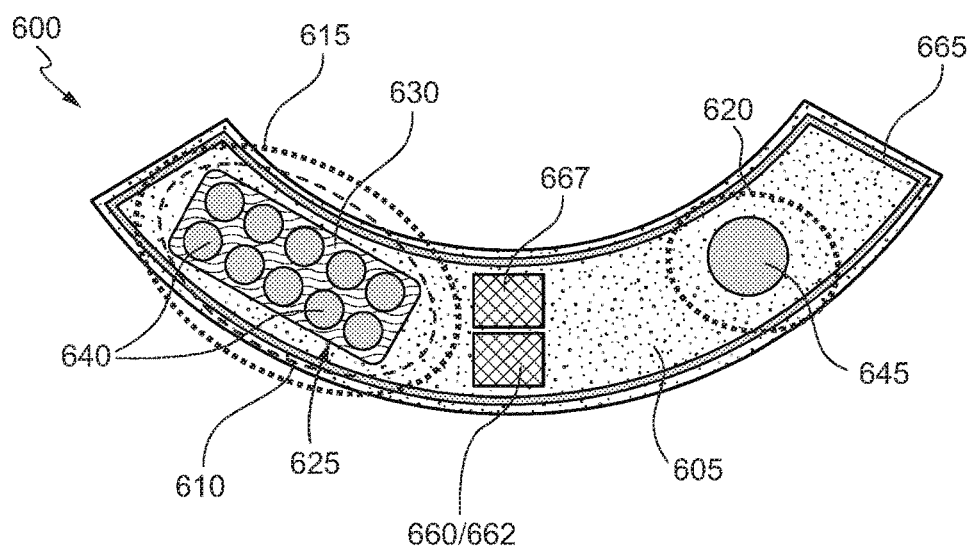

As shown in FIG. 6F, the device 600 may comprise a single reservoir 625 that at least partially overlaps or is otherwise co-located with the iontophoretic delivery region 615. The reservoir 625 may release therapeutic agent 630 via the controlled release mechanism 635 into the iontophoretic delivery region 615 where the therapeutic agent 630 may be driven into the tissue 632. The delivery region 615 comprises a first electrode chamber having multiple first iontophoretic electrodes 640 (e.g., multiple anode electrodes). Release from the reservoir 625 may be active, passive, or combination thereof. The receiving region 620 is located on an opposing end of the device 600 to ensure outward electromigration of the therapeutic agent 630 from the delivery region 615 into the tissue. The receiving region 620 comprises a second electrode chamber having at least one second iontophoretic electrode 645 (e.g., a single cathode electrode or multiple cathode electrodes).

Figure 6G:
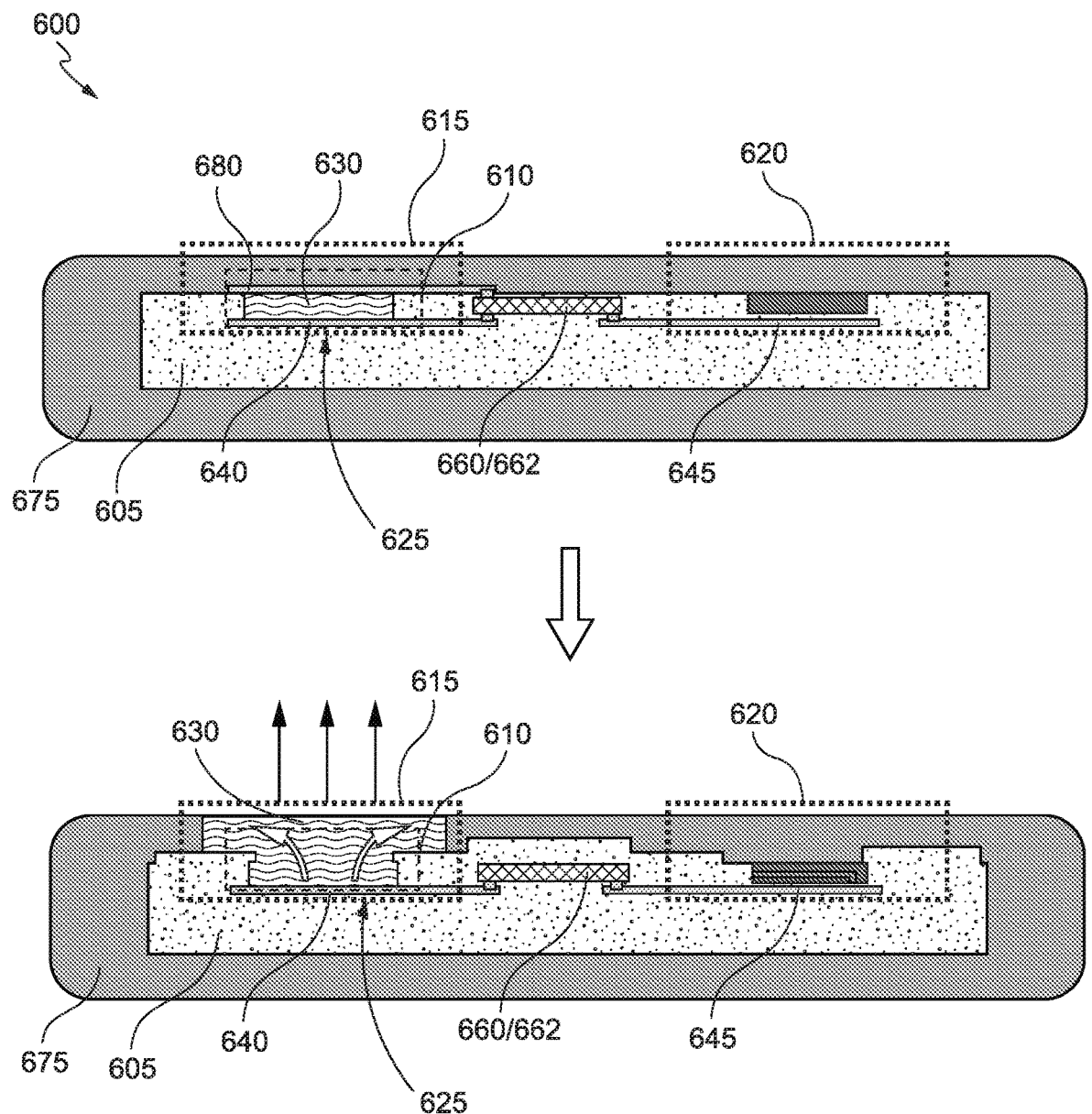

As shown in FIG. 6G, the device 600 may further include an overmold polymeric layer 675 formed around substantially an entirety of the polymeric substrate 605. In some embodiments, the polymeric substrate 605 is fully encapsulated by the overmold polymeric layer 675. In other embodiments, the device 600 includes exposed access points or openings in the overmold polymeric layer 675 (e.g., hydrogel), which exposes a surface of the one or more reservoirs 625 (not shown in FIG. 6G but see, e.g., FIG. 2E). The overmold polymeric layer 675 may be formed of polymethylmethacrylate, polyhydroxyethylmethacrylate, a hydrogel, a silicon-based polymer, a silicone elastomer, or a combination thereof. In certain embodiments, the overmold polymeric layer 675 has a water content between 30% and 50%, for example about 45% water content. In some embodiments, the controlled release mechanism 635 is a combination of a metallic thin film 680 and the overmold polymer layer 675 (a polymeric passive device). The therapeutic agent 630 may be encapsulated or provided behind the metallic thin film 685 (e.g., encapsulated or closed off within the reservoir by a metallic layer that acts as a valve). Once the metallic thin film 680 is opened via external stimulus and dissolution, the therapeutic agent 630 may be released out of the holding chamber of the reservoir 625 through the egress into the overmold polymeric layer 675, as shown in FIG. 6G. Once the therapeutic agent 630 passes through the overmold polymeric layer 675 (e.g., via diffusion or osmotic pump), the therapeutic agent 630 may be released to a delivery region 615. The delivery region 615 comprises a first electrode chamber having multiple first iontophoretic electrodes 640 (e.g., multiple anode electrodes). The receiving region 620 is located on an opposing end of the device 600 to ensure outward electromigration of the therapeutic agent 630 from the delivery region 615 into the tissue. The receiving region 620 comprises a second electrode chamber having at least one second iontophoretic electrode 645 (e.g., a single cathode electrode or multiple cathode electrodes).

While various embodiments are disclosed herein with respect to an eye mountable subtarsal (under eyelid) therapeutic agent release device with facilitated delivery, this is not intended to be restrictive. In addition to providing for customized on-demand scleral therapeutic agent release and delivery, the teachings disclosed herein can also be applied to other therapeutic agent release and delivery devices for other tissues. For example, the therapeutic agent delivery device may be designed to fit discreetly over at least a portion of the corneal surface such that the device does not block or affect vision in any way and is compatible with standard contact lens materials while maintaining preferential contact to the cornea for therapeutic agent delivery to the posterior segment of the eye. Examples of posterior segment diseases where this type of device is of therapeutic benefit include, but are not limited to, macular degeneration, diabetic retinopathy, retinitis pigmentosa, retinal vein occlusions, sickle cell retinopathy, glaucoma, choroidal neovascularization, retinal neovascularization, retinal edema, retinal ischemia, and proliferative vitreoretinopathy.

Corneal Therapeutic Agent Release Device with Facilitated Delivery

The cornea is an effective barrier made of a lipophilic epithelium and a hydrophilic stroma. This makes the cornea very difficult for any molecule therapeutic agents to passively penetrate all the way through the cornea for delivery of agent to the posterior segment; for example, if lipophilic epithelium does not block the therapeutic agent, the hydrophilic stroma will block the therapeutic agent. Therapeutic agents have been developed called prodrugs to overcome this obstacle by having a small molecular weight and the ability to change form (from lipophilic to hydrophilic) as the drug passively passes through the cornea. This results in the slow release of significant concentrations of drug into the aqueous humor for treatment of diseases like macular degeneration, diabetic retinopathy, retinitis pigmentosa, retinal vein occlusions, sickle cell retinopathy, glaucoma, choroidal neovascularization, retinal neovascularization, retinal edema, retinal ischemia, and proliferative vitreoretinopathy. However, in situations where non-prodrug or large molecule therapies are required, the cornea still presents a substantial barrier to effective treatment. Accordingly, in various embodiments, an eye mountable corneal (over the cornea similar to a contact lens) medical device is provided for customized on-demand iontophoretic therapeutic agent delivery.

Figure 7A:
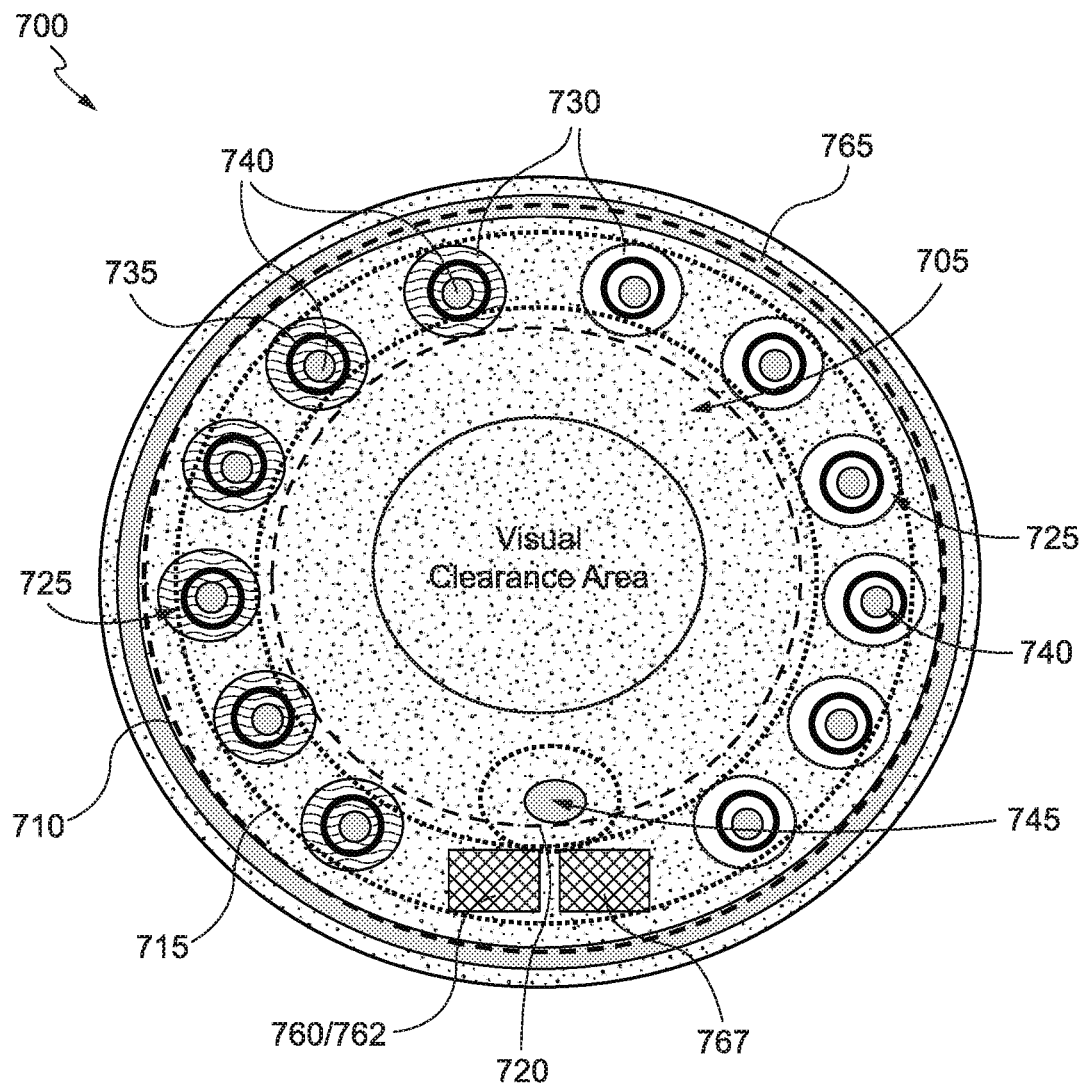
FIGS. 7A-7D show a corneal therapeutic agent release device with facilitated delivery in accordance with various embodiments.

As shown in FIG. 7A, a therapeutic agent delivery device 700 (e.g., a corneal iontophoretic therapeutic agent delivery device) may include a polymeric substrate 705 comprising a release region 710, a delivery region 715, and a receiving region 720. The polymeric substrate 705 may be formed of polyimide, liquid crystal polymer, parylene, polyether ether ketone, polyethylene terephthalate, poly(methyl methacrylate), polyurethane, rigid gas permeable fluorosilicone acrylate, a silicon-based polymer, a silicone acrylate, cyclic olefin co-polymer (COP/COC), a hydrogel, or a combination thereof. In some embodiments, the polymeric substrate 705 has an average thickness (a thickness along an entire length or diameter of the device) between 0.01 mm and 2 mm, for example about 1 mm. In some embodiments, the therapeutic agent delivery device 200 has an average thickness (a thickness along an entire length or diameter of the device) between 0.01 mm and 3 mm, for example about 1.5 mm. The polymeric substrate 705 has a shape and sufficient flexibility for mounting to the contour of the tissue such as the eye. In certain embodiments, the shape is a donut shape as shown in FIG. 7A.

The release region 710 includes one or more areas of the device 700 that support a plurality of reservoirs 725, a therapeutic agent 730 disposed within the one or more of reservoirs 725, and an active, passive, or combination thereof controlled release mechanism 735 for release of the therapeutic agent 730 from each of the one or more of reservoirs 725 into the delivery region 715. The delivery region 715 includes one or more areas of the device 700 that support one or more chambers or compartments (e.g., anode chambers) that comprise one or more first iontophoresis electrodes 740 (e.g., anodes) for transport of the therapeutic agent 730 from the delivery region 715 into a target tissue 732 (e.g., the vitreous humor) via electromigration. The receiving region 720 includes one or more areas of the device 700 that support one or more chambers or compartments (e.g., cathode chambers) that comprise one or more second iontophoresis electrodes 745 (e.g., cathodes) for maintaining electroneutrality within the tissue 732 (e.g., the sclera). As many of the features (e.g., the polymeric substrate 705, the release region 710, the one or more reservoirs 725, the therapeutic agent 730, the active, passive, or combination thereof controlled release mechanism 735, delivery region 715, the receiving region 720, the first iontophoresis electrode 740, and the second iontophoresis electrode 745) of device 700 are the same as the features described with respect to device 200 and 600 in FIGS. 2A-2D and 6A-6G, respectively, the detailed description of such features is not repeated here for brevity.

Figure 7B:
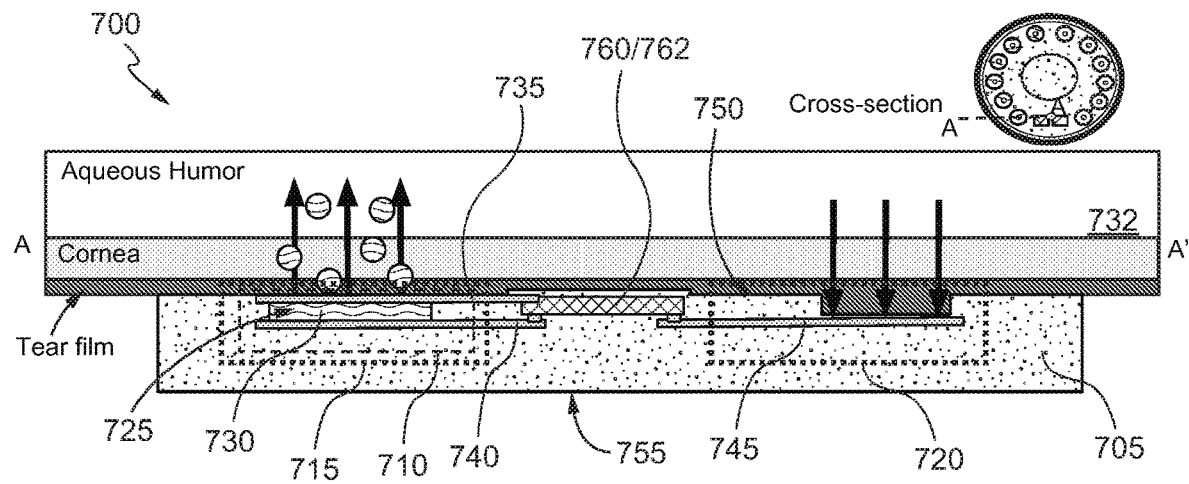

FIG. 7B shows a cross-section of the device 700 with the release region 710 and the delivery region 715 at least partially overlapping or otherwise being co-located within the polymeric substrate 705. The release region 710 and the delivery region 715 are located around an outer perimeter of the device 700, while the receiving region 720 is disposed off-center inside the outer perimeter are encompassing the release region 710 and the delivery region 715. In some embodiments, the polymeric substrate 705 comprises a distal surface 750 and a proximal surface 755 with one or more layers of polymer disposed therebetween. For example, the distal surface 750 may be in contact with a surface of the tissue 732 (posterior), and the proximal surface 755 may be exposed from or not in contact with the surface of the tissue 732 (anterior). In some embodiments, therapeutic agent release is preferentially targeted on the cornea or tissue contacting surface therefore no agent is wasted to the proximal surface 755 or anterior side where agent can be lost to tear efflux and drainage. This results in greater efficacy while eliminating unintended systemic side effects.

In various embodiments, the one or more reservoirs 725 are integrated with or formed within the one or more layers of the polymer. The one or more reservoirs 725 may comprise a holding chamber for the therapeutic agent 730 and an egress for release of the therapeutic agent 730 from the holding chamber. The one or more reservoirs 725 are compatible with various physical forms of therapeutic agents including aqueous (liquid), gel, dry (powder), or other combinations thereof. In some embodiments, the one or more reservoirs 725 provide a means for temporary storage of one or more types of therapeutic agents to allow for on-demand release and delivery of the therapeutic agents at a programmed time with a controlled rate thereby providing a therapeutic effect on the eye via transscleral delivery. FIG. 7A, shows the device 700 configured with two different mono-therapies or types of therapeutic agents in the management of anterior segment disease (e.g., glaucoma). The first type of therapeutic agent (shown on left side of device 700) and the second type of therapeutic agent (shown on right side of device 700) can be packaged and stored in microreservoirs situated within the substrate 705. For example, a first type of therapeutic agent 730 may be disposed within a first subset of the plurality of reservoirs 725 and a second type of therapeutic agent 730 may be disposed within a second subset of the plurality of reservoirs 725. The desired therapeutic agent (first or second) can be released from the individual reservoirs at programmed times and driven into the cornea via iontophoresis (anode and cathode locations shown). In some embodiments, each reservoir holds a single type of therapeutic agent (same or different from other reservoirs). In other embodiments, each reservoir holds multiple types of therapeutic agents (same or different from other reservoirs). The one or more reservoirs 725 may have a volume from 0.01 nL to 100 µL, for example from 0.01 nL to 10.0 µL or about 1.0 µL, and stores a known quantity or volume of therapeutic agent. The one or more reservoirs 725 may be lined with a passive, hermetic, insulator, and/or inert coating such as a dielectric (e.g., $SiO_2$, $Al_2O_3$), or other approved agent-contacting material.

As shown in FIGS. 7A and 7B, the device 700 may further include a power source 760, a capacitor 762, a communications device 765 (e.g., a WiFi antenna), and an electronics module 767 (i.e., hardware, software or a combination thereof). The power source 760 may be connected (e.g., electrically connected) to the electronics module 767 to power and operate the components of the electronics module 767. The power source 760 may be connected (e.g., electrically connected) to the capacitor 762 to power and provide current flow for one or more circuits 770. The communications device 765 may be connected (e.g., electrically connected) to the electronics module 767 for wired or wireless communication with external devices via, for example, radiofrequency (RF) telemetry or WiFi. The electronics module 767 may be connected (e.g., electrically connected) to the capacitor 762 and the one or more circuits 770 such that the electronics module 767 is able to apply a signal or electrical current to electronic components such as gates, electrodes, or sensors connected to the one or more circuits 770. In some embodiments, the one or more circuits 770 include a current source (e.g., the power source 760 and the capacitor 762), the first iontophoresis electrodes 740 located within the delivery region 715 for transport of the therapeutic agent 730 from the delivery region 615 into a target tissue 732 via electromigration, and a second iontophoresis electrode 745 located within the receiving region 720 for maintaining electroneutrality within the tissue 732.

In various embodiments, the device 700 achieves release of the therapeutic agent 730 from the one or more reservoirs 725 to the delivery region 715 or an interface with the tissue 732 via the active, passive, or combination thereof controlled release mechanism 735 (see, e.g., FIG. 7B). In some embodiments, the one or more reservoirs 725 comprises the holding chamber for the therapeutic agent 730, the egress, and the active, passive, or combination thereof controlled release mechanism 735 that temporarily blocks passage of the therapeutic agent 730 from the holding chamber through the egress. In some embodiments, the controlled release mechanism 735 is a passive polymer device (or device constructed of a similar material). In some embodiments, the controlled release mechanism 735 is an active polymer device (or device constructed of a similar material). In some embodiments, the controlled release mechanism 735 is an active metal device (or device constructed of a similar material). In some embodiments, the controlled release mechanism 735 is a combination of one or more passive devices and one or more active devices. In some embodiments, the controlled release mechanism 735 is a passive polymer device (or device constructed of a similar material) and an active polymer or metal device.

In some embodiments, the release region 710 and the delivery region 715 are in fluidic communication. For example, once the therapeutic agent 730 is released from the one or more reservoirs 725 via the active, passive, or combination thereof controlled release mechanism 735, the therapeutic agent 730 is capable of flowing into the delivery region 715 or an interface with the tissue 732. In certain embodiments, at least a portion of the delivery region 715 is exposed to an environment external to the polymeric substrate 705. The external environment may be a tissue interface such as an interface between the polymeric substrate 705 and the tear film or corneal surface. In some embodiments, one or more first electrode chambers such as anode chamber is formed within the one or more layers of polymer (e.g., within a delivery region 715) and in fluidic communication with the one or more reservoirs 725. The one or more first electrode chambers comprise the first iontophoresis electrode 740. In certain embodiments, the first iontophoresis electrode 740 is located under the one or more reservoirs 725 formed within the release region 710 of the polymeric substrate 705. Moreover, at least a portion of the one or more first electrode chambers is exposed to an environment external to the polymeric substrate 705 at the distal surface 750. The one or more first electrode chambers are capable of receiving the therapeutic agent 730 from the reservoir upon release of the therapeutic agent 730 via the active, passive, or combination thereof controlled release mechanism 735. The therapeutic agent 730 may be ionizable, and a counter ion (the counter ion has a charge opposite that of the therapeutic agent 730) may be disposed within the one or more reservoirs 725 or the one or more first electrode chambers (e.g., within a delivery region 715). In some embodiments, a second electrode chamber such as cathode chamber is formed within the one or more layers of polymer (e.g., within a receiving region 720) and at least a portion of the second electrode chamber is exposed to an environment external to the polymeric substrate 705 at the distal surface 750. The second electrode chamber comprises the second iontophoresis electrode 745.

Figure 7C:
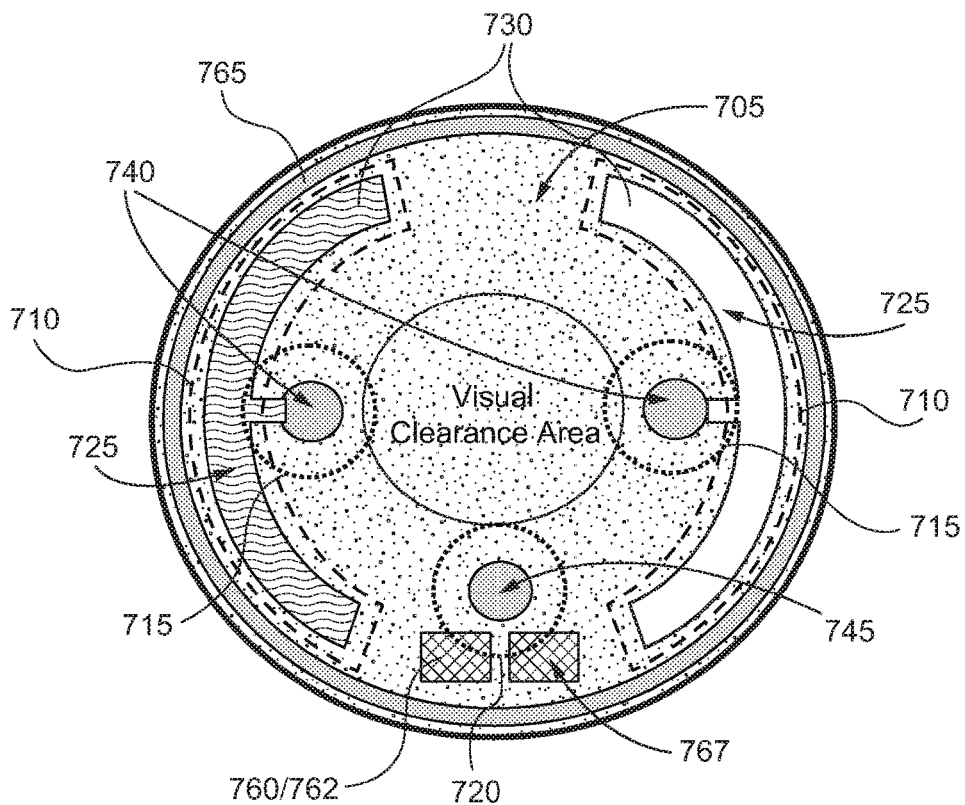

As shown in FIG. 7C, the device 700 may comprise therapeutic agent storage 730 in the one or more reservoirs 725 located separately from one or more iontophoretic delivery regions 715. The one or more reservoirs 725 may release therapeutic agent 730 via the controlled release mechanism 735 into the one or more iontophoretic delivery regions 715 where the therapeutic agent 730 may be driven into the tissue 732. Each of the delivery regions 715 comprise a first electrode chamber having at least one first iontophoretic electrode 740 (e.g., a single anode electrode or multiple anode electrodes). Release from the one or more reservoirs 725 may be active, passive, or combination thereof. The receiving region 720 is located off-center of the device 700 to ensure outward electromigration of the therapeutic agent 730 from the one or more delivery regions 715 into the tissue. The receiving region 720 comprises a second electrode chamber having at least one second iontophoretic electrode 745 (e.g., a single cathode electrode or multiple cathode electrodes).

Figure 7D:
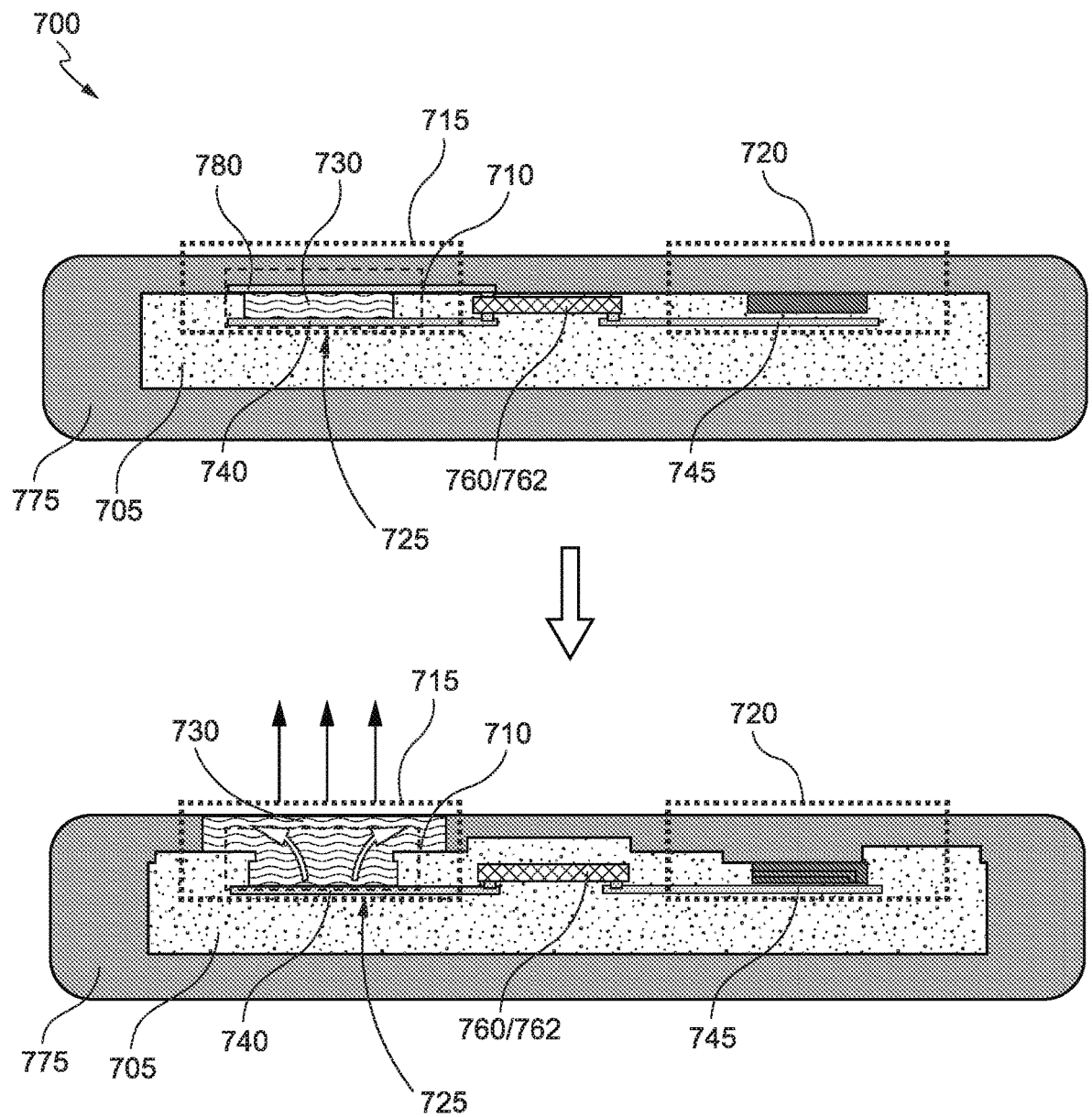

As shown in FIG. 7D, the device 700 may further include an overmold polymeric layer 775 formed around substantially an entirety of the polymeric substrate 705. In some embodiments, the polymeric substrate 705 is fully encapsulated by the overmold polymeric layer 775. In other embodiments, the device 700 includes exposed access points or openings in the overmold polymeric layer 775 (e.g., hydrogel), which exposes a surface of the one or more reservoirs 725 (not shown in FIG. 7D but see, e.g., FIG. 2E). The overmold polymeric layer 775 may be formed of polymethylmethacrylate, polyhydroxyethylmethacrylate, a hydrogel, a silicon-based polymer, a silicone elastomer, or a combination thereof. In certain embodiments, the overmold polymeric layer 775 has a water content between 30% and 50%, for example about 45% water content. In some embodiments, the controlled release mechanism 635 is a combination of a metallic thin film 780 and the overmold polymer layer 775 (a polymeric passive device). The therapeutic agent 730 may be encapsulated or provided behind the metallic thin film 785 (e.g., encapsulated or closed off within the reservoir by a metallic layer that acts as a valve). Once the metallic thin film 780 is opened via external stimulus and dissolution, the therapeutic agent 730 may be released out of the holding chamber of the reservoir 725 through the egress into the overmold polymeric layer 775, as shown in FIG. 7D. Once the therapeutic agent 730 passes through the overmold polymeric layer 775 (e.g., via diffusion or osmotic pump), the therapeutic agent 730 may be released to a delivery region 715. The delivery region 715 comprises a first electrode chamber having multiple first iontophoretic electrodes 740 (e.g., multiple anode electrodes). The receiving region 720 is located off-center of the device 700 to ensure outward electromigration of the therapeutic agent 730 from the delivery region 715 into the tissue. The receiving region 720 comprises a second electrode chamber having at least one second iontophoretic electrode 745 (e.g., a single cathode electrode or multiple cathode electrodes).

III. Systems for Therapeutic Agent Release and Delivery

Figure 8:
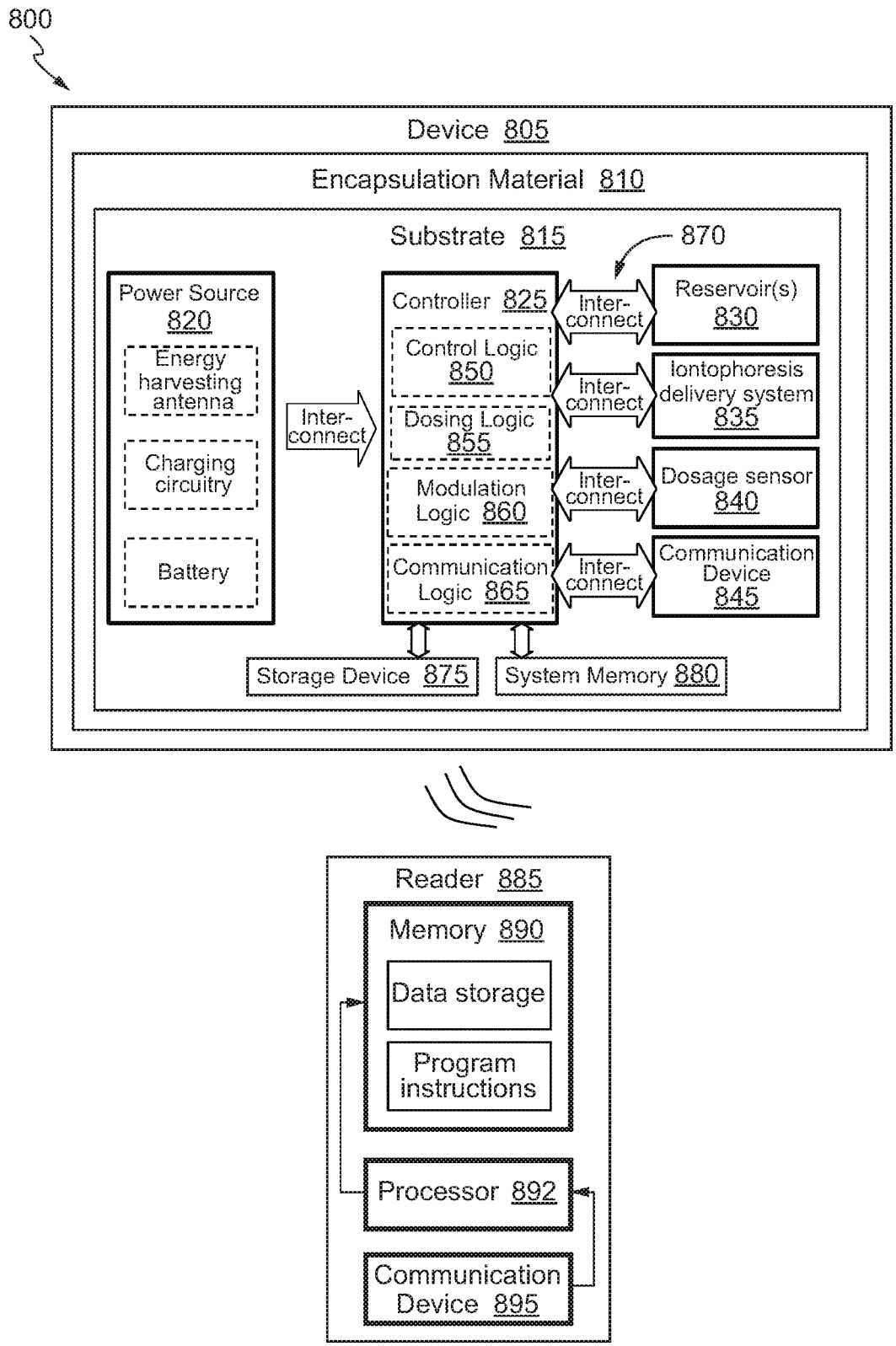
FIG. 8 shows a system for therapeutic agent release and delivery in accordance with various embodiments.

FIG. 8 shows a therapeutic agent release and delivery system 800 in accordance with various embodiments. In some embodiments, the therapeutic agent release and delivery system 800 includes one or more delivery devices 805 (e.g., device 200/600/700 described with respect to FIGS. 2A-2E, 6A-6G, and 7A-7D, respectively), an optional encapsulation layer 810 (e.g., the overmold polymeric layer 290/675/775 described with respect to FIGS. 2A-2E, 6A-6G, and 7A-7D, respectively), and a substrate 815 (e.g., the polymeric substrate 205/605/705 described with respect to FIGS. 2A-2E, 6A-6G, and 7A-7D, respectively. In certain embodiments, the therapeutic agent release and delivery system 800 is disposed on one or both eyes of a patient. The substrate 815 includes software and/or electronic circuit components that provide active or customized on-demand iontophoretic transscleral or transcorneal therapeutic agent delivery. The software and/or electronic circuit components includes a power source 820 (e.g., power source 250/660/760 described with respect to FIGS. 2A-2E, 6A-6G, and 7A-7D, respectively), a controller 825 (e.g., electronics module 270/667/767 described with respect to FIGS. 2A-2E, 6A-6G, and 7A-7D, respectively), the one or more reservoirs 830 (e.g., the reservoirs 215/625/725 described with respect to FIGS. 2A-2E, 6A-6G, and 7A-7D, respectively), the iontophoresis electrode delivery system 835 (e.g., the electrode delivery system described with respect to 6A-6G and 7A-7D, respectively), one or more dosage sensors 840, and the communications device 845 (e.g., communications device 265/665/765 described with respect to FIGS. 2A-2E, 6A-6G, and 7A-7D, respectively).

In certain embodiments, the controller 825 includes one or more conventional processors, microprocessors, or specialized dedicated processors that include processing circuitry operative to interpret and execute computer readable program instructions, such as program instructions for controlling the operation and performance of one or more of the various other components of device 805 for implementing the functionality, steps, and/or performance of the present embodiments. In certain embodiments, the controller 825 interprets and executes the processes, steps, functions, and/or operations of the present invention, which may be operatively implemented by the computer readable program instructions. For example, the controller 825 includes control logic 845, dosing logic 850, modulation logic 855, and communication logic 860 that communicate interactively via one or more circuits 865 with the one or more reservoirs 830, the iontophoresis electrode delivery system 835, the one or more dosage sensors 840, and the communications device 845. In some embodiments, the information obtained or generated by the controller 825, e.g., the status of agent delivery, agent dosages, temporal location in therapeutic window, etc., can be stored in the storage device 870.

The storage device 870 may include removable/non-removable, volatile/non-volatile computer readable media, such as, but not limited to, non-transitory machine readable storage medium such as magnetic and/or optical recording media and their corresponding drives. The drives and their associated computer readable media provide for storage of computer readable program instructions, data structures, program modules and other data for operation of the controller 825 in accordance with the different aspects of the present invention. In some embodiments, the storage device 870 stores an operating system, application programs, and program data.

A system memory 875 may include one or more storage mediums, including for example, non-transitory machine readable storage medium such as flash memory, permanent memory such as read-only memory ("ROM"), semi-permanent memory such as random access memory ("RAM"), any other suitable type of non-transitory storage component, or any combination thereof. In some embodiments, an input/output system (BIOS) including the basic routines that help to transfer information between the various other components of device 805, such as during start-up, may be stored in the ROM. Additionally, data and/or program modules, such as at least a portion of operating system, program modules, application programs, and/or program data, that are accessible to and/or presently being operated on by one or more processors, may be contained in the RAM. In embodiments, the program modules and/or application programs can comprise, for example, control logic 845, dosing logic 850, modulation logic 855, and communication logic 860, which provides the instructions for execution of the one or more processors.

The communication device 845 may include any transceiver-like mechanism (e.g., a network interface, a network adapter, a modem, or combinations thereof) that enables device 805 to communicate with remote devices or systems, such as a mobile device or other computing devices such as, for example, a server in a networked environment, e.g., cloud environment. For example, device 805 may be connected to remote devices or systems via one or more local area networks (LAN) and/or one or more wide area networks (WAN) using communication device 845.

The controller 825 can be remotely accessed following implant through an external programmer or reader 845, such as an external computing device. For example, the external programmer or reader 845 can be used by healthcare professionals to check and program the controller 825 before or after distribution to a patient (e.g., while the patient is wearing the device 805), adjust release and delivery parameters during a delivery process, e.g., providing an initial set of the release and delivery parameters, and read any data concerning dosage, delivery, and compliance of the device during or after a dosing regimen. In some embodiments, the external programmer or reader 845 comprises a memory 850 (e.g., a storage device or system memory), one or more processors 855, and a communications device such as a WiFi antenna. The external programmer or reader 845 may communicate with the controller 825 via wired or wireless communication methods, such as, e.g., wireless radio frequency transmission.

As discussed herein, the system 800 may be configured to control release of a therapeutic agent from one or more reservoirs into a delivery region, and control application of a potential to a circuit to create a current flowing through the circuit that causes electromigration of the therapeutic agent from the delivery region to a tissue. In particular, device 800 may perform tasks (e.g., process, steps, methods and/or functionality) in response to controller 825 executing program instructions contained in non-transitory machine readable storage medium, such as system memory 875. The program instructions may be read into system memory 875 from another computer readable medium (e.g., non-transitory machine readable storage medium), such as data storage device 870, or from another device such as external programmer or reader 845 via the communication device 845 or server within or outside of a cloud environment. In some embodiments, an operator may interact with external programmer or reader 845 via one or more input devices and/or the one or more output devices to facilitate performance of the tasks and/or realize the end results of such tasks in accordance with various aspects described herein. In additional or alternative embodiments, hardwired circuitry may be used in place of or in combination with the program instructions to implement the tasks, e.g., steps, methods and/or functionality, consistent with the different aspects. Thus, the steps, methods and/or functionality disclosed herein can be implemented in any combination of hardware circuitry and software.

Figure 9:
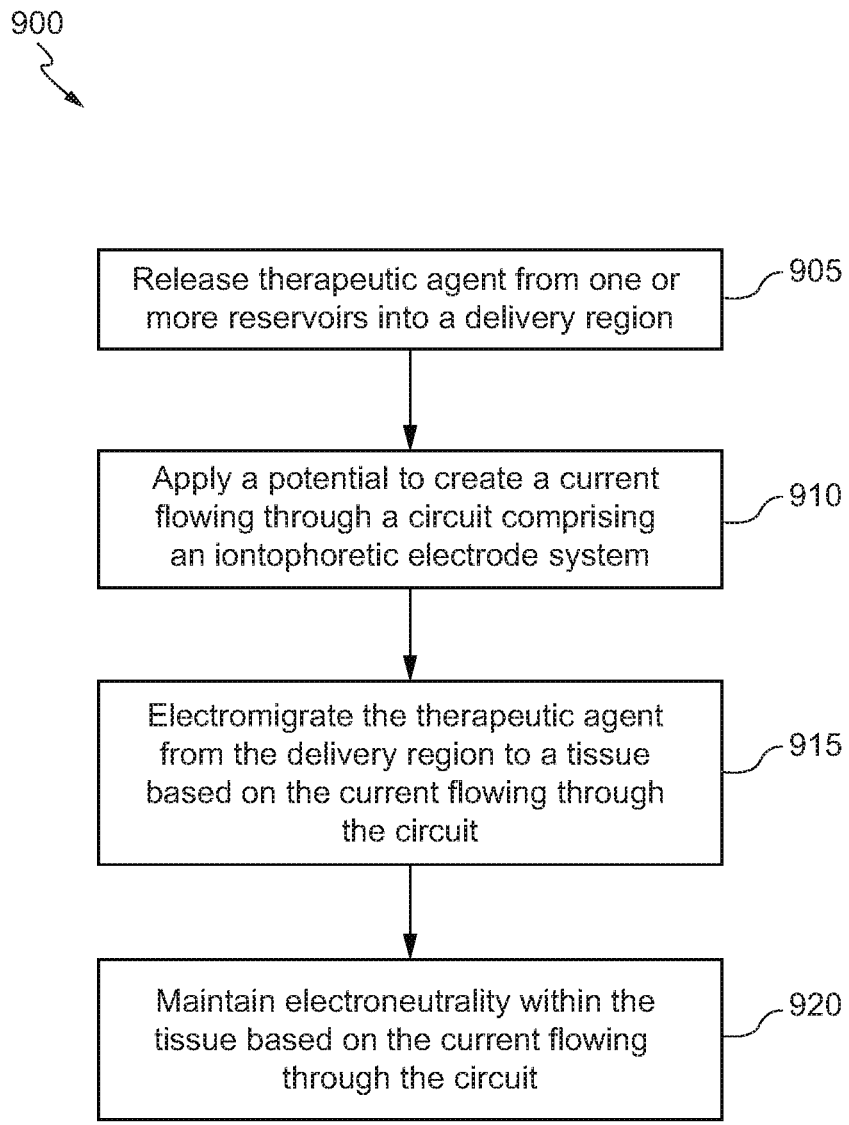
FIG. 9 shows a flow diagram of a process for therapeutic agent release and delivery in accordance with various embodiments.

FIG. 9 depicts a simplified flowchart depicting processing performed for release and delivery of a therapeutic agent according to various embodiments. The steps of FIG. 9 may be implemented in the device and system environments of FIGS. 2A-2E, 6A-6G, 7A-7D, and 8, for example. As noted herein, the flowchart of FIG. 9 illustrates the architecture, functionality, and operation of possible implementations of systems, methods, and computer program products according to various embodiments of the present invention. In this regard, each block in the flowchart or block diagrams may represent a module, segment, or portion of code, which comprises one or more executable instructions for implementing the specified logical functions. It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combination of blocks in the block diagrams and/or flowchart illustration, can be implemented by special purpose hardware-based systems that perform the specified functions or acts, or combinations of special purpose hardware and computer instructions.

With reference to FIG. 9, at step 905, a therapeutic agent is release from one or more reservoirs formed within a release region of the polymeric substrate into a delivery region of the polymeric substrate. In some embodiments, the release is caused by the controller activating a controlled release mechanism or valve to open. For example, the releasing may comprise applying, by the controller, a potential to the controlled release mechanism. At step 910, a potential (different from the potential that causes release of the agent from the reservoirs) may be applied to a circuit formed on the polymeric substrate to create a current flowing through the circuit, where the circuit comprises a current source, a first iontophoresis electrode located within the delivery region, and a second iontophoresis electrode located within a receiving region of the polymeric substrate. At step 915, the therapeutic agent may undergo electromigration, by the first iontophoresis electrode, from the delivery region to a tissue based on the current flowing through the circuit. For example, application of the electric potential causes a current to flow through the circuit. At an electrode solution interface, the ions such as Ag+ and Cl− react to form insoluble AgCl which is deposited on the electrode surface. Electromigration transports the cations, including the therapeutic agent from the anodal compartment and into the tissue. At step 920, electroneutrality may be maintained, by the second iontophoresis electrode, within the tissue based on the current flowing through the circuit. For example, in the cathodal chamber, ions such as Cl− ions are released from the second iontophoresis electrode and electroneutrality requires that either an anion is lost from the cathodal chamber or that a cation enters the chamber from the tissue. The extent and penetration depth of iontophoretic delivery is related to the electric field and the duration of application of the potential. Steps 905-920 may be repeated as necessary for active release and delivery of one or more therapeutic agents for maintaining physiologically relevant concentrations in conditions with a static or time-varying therapeutic window.

While the invention has been described in detail, modifications within the spirit and scope of the invention will be readily apparent to the skilled artisan. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by the skilled artisan. Furthermore, the skilled artisan will appreciate that the foregoing description is by way of example only, and is not intended to limit the invention.

What is claimed is:

1. A therapeutic agent delivery device comprising a polymeric substrate, wherein the polymeric substrate comprises:
   a release region comprising:
      one or more reservoirs configured to hold a therapeutic agent,
      a mechanism configured to control a release of the therapeutic agent from the one or more reservoirs;
   a delivery region in fluid communication with the release region configured to receive the therapeutic agent released from the one or more reservoirs, comprising a first ionophoresis electrode configured to transport the therapeutic agent released from the one or more reservoirs into a target tissue via electromigration, and
   a receiving region comprising a second iontophoresis electrode configured to maintain electroneutrality within the target tissue,
   wherein a circuit is formed between a current source, the first iontophoresis electrode, and the second ionophoresis electrode.

2. The therapeutic agent delivery device of claim 1, wherein the mechanism is an active controlled release mechanism and/or a passive controlled release mechanism.

3. The therapeutic agent delivery device of claim 1, wherein the current source is formed on the polymeric substrate.

4. The therapeutic agent delivery device of claim 1, wherein the current source is formed within the polymeric substrate.

5. The therapeutic agent delivery device of claim 1, wherein the first iontophoresis electrode comprises an anode and the second iontophoresis electrode comprises a cathode.

6. The therapeutic agent delivery device of claim 1, wherein the polymeric substrate comprises a distal surface and a proximal surface with one or more layers of polymer disposed between the distal surface and the proximal surface.

7. The therapeutic agent delivery device of claim 1, wherein the target tissue is a vitreous humor, a sclera, or a cornea.

8. The therapeutic agent delivery device of claim 1, wherein the release region and the delivery region at least partially co-located within the polymeric substrate.

9. The therapeutic agent delivery device of claim 1, wherein the release region and the delivery region are located in different locations within the polymeric substrate.

10. The therapeutic agent delivery device of claim 1, wherein the therapeutic agent is provided in a liquid from, a gel form, and/or a powder form.

11. The therapeutic agent delivery device of claim 1, wherein the one or more reservoirs comprise a plurality of reservoirs each configured to house the therapeutic agent.

12. The therapeutic agent delivery device of claim 1, wherein the one or more reservoirs comprise a plurality of reservoirs each configured to house a different therapeutic agent.

13. The therapeutic agent delivery device of claim 1, wherein the polymeric substrate comprises at least one of a polyimide, a liquid crystal polymer, a parylene, a polyether ether ketone, a polyethylene terephthalate, a poly(methyl methacrylate), a polyurethane, a rigid gas permeable fluorosilicone acrylate, a silicon-based polymer, a silicone acrylate, a cyclic olefin co-polymer (COP/COC), and a hydrogel.

14. The therapeutic agent delivery device of claim 1, wherein the release region comprises a single reservoir that is located separate from the first delivery region.

15. The therapeutic agent delivery device of claim 1, wherein the release region comprises a single reservoir that is located in contact with the delivery region.

16. The therapeutic agent delivery device of claim 1, wherein the first ionophoresis electrode comprises a silver electrode and the second ionophoresis electrode comprises a silver chloride electrode.

17. The therapeutic agent delivery device of claim 1, wherein the mechanism comprises a metallic thin film electronically connected to the current source.

18. The therapeutic agent delivery device of claim 17, wherein the mechanism further comprises a valve.

19. The therapeutic agent delivery device of claim 1, further comprising one or more processors formed on or within the polymeric substrate and electrically connected to the current source; a battery formed on or within the polymeric substrate and electrically connected to the current source; and an antenna formed on or within the polymeric substrate and electrically connected to the one or more processors.

20. The therapeutic agent delivery device of claim 1, further comprising an overmold polymeric layer formed around the polymeric substrate.

21. The therapeutic agent delivery device of claim 20, wherein the overmold polymeric layer leaves one or more access points of the polymer substrate exposed.

* * * * *